United States Patent
Ouyang et al.

(10) Patent No.: US 11,964,262 B2
(45) Date of Patent: *Apr. 23, 2024

(54) PHOSPHORUS-CONTAINING RARE-EARTH-CONTAINING MFI STRUCTURE MOLECULAR SIEVE RICH IN MESOPORE, PREPARATION METHOD, AND CATALYST CONTAINING SAME AND APPLICATION THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Ying Ouyang, Beijing (CN); Yibin Luo, Beijing (CN); Jianqiang Liu, Beijing (CN); Li Zhuang, Beijing (CN); Minggang Li, Beijing (CN); Xingtian Shu, Beijing (CN)

(73) Assignees: CHINA PETROLEUM & CHEMICAL CORPORATION, Bejing (CN); RESEARCH INSTITUTE OF PETROLEUM PROCESSING, SINOPEC, Beijing (CN)

(*) Notice: Subject to any disclaimer, the term of this patent is extended or adjusted under 35 U.S.C. 154(b) by 281 days.

This patent is subject to a terminal disclaimer.

(21) Appl. No.: 17/286,758

(22) PCT Filed: Oct. 17, 2019

(86) PCT No.: PCT/CN2019/111740
§ 371 (c)(1),
(2) Date: Apr. 19, 2021

(87) PCT Pub. No.: WO2020/078437
PCT Pub. Date: Apr. 23, 2020

(65) Prior Publication Data
US 2021/0387171 A1    Dec. 16, 2021

(30) Foreign Application Priority Data

Oct. 18, 2018 (CN) .......................... 201811217720.8
Feb. 19, 2019 (CN) .......................... 201910123049.9
Jun. 28, 2019 (CN) .......................... 201910578658.3
Jun. 28, 2019 (CN) .......................... 201910580180.8

(51) Int. Cl.
*B01J 29/064*  (2006.01)
*B01J 29/035*  (2006.01)
(Continued)

(52) U.S. Cl.
CPC ........... *B01J 29/46* (2013.01); *B01J 29/0352* (2013.01); *B01J 29/0356* (2013.01);
(Continued)

(58) Field of Classification Search
CPC ... C01B 39/026; C01B 39/24; C01P 2002/01; C01P 2006/12; C01P 2006/14; C01P 2006/16; C10G 11/05; C10G 2400/20; C10G 2400/30; B01J 21/04; B01J 21/16; B01J 27/16; B01J 27/18; B01J 37/0009; B01J 37/0045; B01J 37/10; B01J 37/02; B01J 37/28; B01J 35/0073; B01J 35/0093; B01J 35/0086; B01J 35/109; B01J 35/10; B01J 35/1019; B01J 35/1004; B01J 35/1061; B01J 35/1066; B01J 35/1033; B01J 29/084; B01J 29/088; B01J 29/0352;
(Continued)

(56) References Cited

U.S. PATENT DOCUMENTS 3,702,886 A    11/1972    Argauer et al.
3,709,979 A    1/1973     Chu et al.
(Continued)

FOREIGN PATENT DOCUMENTS

CN    1147420 A     4/1997
CN    1072032 C     10/2001
(Continued)

OTHER PUBLICATIONS

Machine Translation of CN 107971015 A, May 1, 2018, pp. 1-37.*
(Continued)

*Primary Examiner* — Elizabeth D Wood
(74) *Attorney, Agent, or Firm* — NKL Law; Allen Xue

(57) ABSTRACT

A rare earth- and phosphorus-containing molecular sieve of MFI structure rich in mesopores has a ratio of $n(SiO_2)/n(Al_2O_3)$ of more than 15 and less than 70. The molecular sieve has a content of phosphorus of 1-15 wt %, calculated as $P_2O_5$ and based on the dry weight of the molecular sieve. The content of the supported metal in the molecular sieve is 1-10 wt % supported metal M1 and 0.1-5 wt % supported metal M2 based on the oxide of the supported metal and the dry weight of the molecular sieve. The supported metal M1 is one or two selected from lanthanum and cerium, and the supported metal M2 is one selected from iron, cobalt, nickel, copper, manganese, zinc, tin, bismuth and gallium; the volume of mesopores in the molecular sieve represents 40-70% by volume of the total pore volume of the molecular sieve by volume.

25 Claims, No Drawings

(51) Int. Cl.
*B01J 29/04* (2006.01)
*B01J 29/08* (2006.01)
*B01J 29/46* (2006.01)
*C07C 4/06* (2006.01)
*C10G 11/05* (2006.01)

(52) U.S. Cl.
CPC ......... *B01J 29/0358* (2013.01); *B01J 29/041* (2013.01); *B01J 29/042* (2013.01); *B01J 29/043* (2013.01); *B01J 29/044* (2013.01); *B01J 29/045* (2013.01); *B01J 29/084* (2013.01); *B01J 29/088* (2013.01); *C07C 4/06* (2013.01); *C10G 11/05* (2013.01); *B01J 2229/42* (2013.01); *B01J 2229/66* (2013.01)

(58) Field of Classification Search
CPC .. B01J 29/0356; B01J 29/0358; B01J 29/041; B01J 29/40; B01J 29/405; B01J 29/42; B01J 29/46; B01J 29/48; B01J 29/80; B01J 2229/186; B01J 2229/20; B01J 2229/26; B01J 2229/24; B01J 2229/40; B01J 2229/42; B01J 2229/38; B01J 29/042; B01J 29/043; B01J 29/044; B01J 29/045
USPC ........ 502/60, 63, 64, 65, 66, 67, 68, 69, 71, 502/72, 73, 74, 77, 79; 208/113, 114, 208/118, 119, 120.01, 121, 122, 124, 208/120.35
See application file for complete search history.

(56) References Cited

U.S. PATENT DOCUMENTS

| | | |
|---|---|---|
| 6,417,421 B1 | 7/2002 | Yao |
| 2015/0165427 A1 | 6/2015 | Awayssa et al. |

FOREIGN PATENT DOCUMENTS

| | | |
|---|---|---|
| CN | 1660967 A | 8/2005 |
| CN | 102049284 A | 5/2011 |
| CN | 104056654 A | 9/2014 |
| CN | 104307560 A | 1/2015 |
| CN | 104549467 A | 4/2015 |
| CN | 104557377 A | 4/2015 |
| CN | 106140270 A | 11/2016 |
| CN | 106552673 A | 4/2017 |
| CN | 106607089 A | 5/2017 |
| CN | 107970990 A | 5/2018 |
| CN | 107971015 A | 5/2018 |
| CN | 107973317 A | 5/2018 |
| CN | 107973318 A | 5/2018 |
| GB | 1334243 A | 10/1973 |

OTHER PUBLICATIONS

Machine Translation of CN 1660967 A, Aug. 31, 2005, pp. 1-15.*
Ebrahim Mohiuddin et al., "The effect of Fe and Cr impregnated ZSM-5 on olefin selectivity", Applied Petrochemical Research (2018), 8:119-129.*

* cited by examiner

PHOSPHORUS-CONTAINING RARE-EARTH-CONTAINING MFI STRUCTURE MOLECULAR SIEVE RICH IN MESOPORE, PREPARATION METHOD, AND CATALYST CONTAINING SAME AND APPLICATION THEREOF

TECHNICAL FIELD

The invention relates to a rare earth- and phosphorus-containing molecular sieve of MFI structure rich in mesopores and a process of producing same, and a catalyst containing the molecular sieve and use thereof.

BACKGROUND

Since the 21$^{st}$ century, the fluctuation of crude oil price and the rapid progress of technology promotes the development of the global petrochemical industry to diversification of raw materials and low cost. Particularly, the rapid expansion of petrochemical production energy in middle east areas rich in light hydrocarbon resources, the development of North American shale gas and the Chinese coal chemical industry and the like, bring great impact to the traditional petrochemical industry taking naphtha as a raw material. The large-scale marketization of the technology for producing ethylene from ethane also brings challenge to the production of low-carbon olefins through steam cracking of naphtha. Relatively, the conventional naphtha route has high economic cost and low competitiveness in the production of ethylene, so that the development of a competitive chemical raw material production technology is concerned.

The cracking reaction of hydrocarbons at high temperature is an important process for converting long-chain hydrocarbons into short-chain hydrocarbons with high added value, particularly low-carbon olefins and gasoline. Generally, the cracking of hydrocarbons can be classified into a carbonium ion mechanism (catalytic cracking) and a radical mechanism (steam cracking) in view of the mechanism. The carbonium ion mechanism needs to act under the action of an acid catalyst, for which the reaction temperature required is relatively low, and the cracking product is characterized by the inclusion of propylene, while the free radical mechanism generally results in reaction under the condition of thermal initiation, and the cracking product is characterized by the inclusion of ethylene. In fact, hydrocarbons undergo both carbonium and free radical reactions under catalytic cracking reaction conditions. However, due to the low reaction temperature, the initiation speed of free radicals is low, such that the reaction process mainly adopts carbonium ion reaction, resulting in a high yield of propylene, and a low yield of ethylene. The ethylene/propylene ratio in the product cannot be finely and freely controlled in a large range at present.

Catalytically thermal cracking of ethylene is a new way to increase the yield of ethylene. The traditional process of producing ethylene by steam cracking has the defects of high cracking temperature, strict requirements on raw materials and the like. It is believed that the steam cracking produces ethylene by a free radical reaction mechanism, and therefore the reaction temperature is high. In the catalytically thermal cracking catalyst for producing a large amount of light olefins, a ZSM-5 molecular sieve is generally used as an active component, and the molecular sieve is adjusted to increase the yield of C3═—C5═olefins, so that the ethylene yield is not very high.

CN1072032C discloses a molecular sieve composition for catalytic cracking to produce ethylene and propylene with a high yield, which is prepared by activating and modifying five-membered ring molecular sieves by P, an alkaline earth metal and a transition metal at a molar ratio of $SiO_2/Al_2O_3$ of 15-60. The modified molecular sieve contains 2-10 wt % of $P_2O_5$, 0.3-5 wt % of alkaline earth metal oxide and 0.3-5 wt % of transition metal oxide. The structure and active center of the molecular sieve have high thermal and hydrothermal stability.

CN1147420A discloses a molecular sieve containing phosphorus and rare earth and having an MFI structure, and the anhydrous chemical composition of the molecular sieve is $aRE_2O_3 bNa_2O Al_2O_3 cP_2O_5 dSiO_2$ wherein a=0.01-0.25, b=0.005-0.02, c=0.2-1.0, and d=35-120. The molecular sieve has excellent hydrothermal activity stability and good low-carbon olefin selectivity when being used for high-temperature conversion of hydrocarbons.

In the prior art, the effect of modulating the properties of the molecular sieve is mostly concentrated on the improvement of the yield and the selectivity of the propylene and the butylene, while the improvement effect of the yield and the selectivity of the ethylene is not obvious enough.

SUMMARY OF THE INVENTION

The invention aims to provide a rare earth- and phosphorus-containing molecular sieve of MFI structure rich in mesopores and a process of producing same. The molecular sieve of MFI structure can show excellent ethylene yield and simultaneously results in high outputs of propylene and BTX in the catalytic cracking of petroleum hydrocarbons.

The invention also aims to provide a catalyst containing the rare earth- and phosphorus-containing molecular sieve of MFI structure rich in mesopores, a process of producing same.

For the purpose above, in a first aspect, the present invention provides a rare earth- and phosphorus-containing molecular sieve of MFI structure rich in mesopores, the molecular sieve comprising a silicon component, an aluminum component, a phosphorus component, and a supported metal component comprising supporting metals M1 and M2, wherein the molecular sieve has a ratio of $n(SiO_2)/n(Al_2O_3)$ of greater than 15 and less than 70; the molecular sieve has a content of phosphorus, calculated as $P_2O_5$, of 1-15 wt % based on the dry weight of the molecular sieve; the molecular sieve has a supported metal content, calculated as the oxide of the supported metal, of 1-10 wt % supported metal M1 and 0.1-5 wt % supported metal M2 based on the dry weight of the molecular sieve, in which the supported metal M1 is one or more selected from rare earth elements, preferably one or two selected from lanthanum and cerium, and the supported metal M2 is one selected from iron, cobalt, nickel, copper, manganese, zinc, tin, bismuth and gallium; and the volume of mesopores in the molecular sieve represents 40-70% by volume of the total pore volume of the molecular sieve, in which the volume of mesopores and the total pore volume of the molecular sieve are measured by a nitrogen adsorption BET specific surface area method, and the volume of mesopores means the pore volume of the pores having a diameter of more than 2 nm and less than 100 nm.

In one embodiment, for the rare earth- and phosphorus-containing molecular sieve of MFI structure rich in mesopores, the molecular sieve has a RE distribution parameter, D, satisfying: 0.9≤D≤1.3, preferably 0.9≤D≤1.1, wherein D=RE (S)/RE (C), RE (S) represents the content of rare earth in any region of more than 100 nm² within an inward distance of H from the edge of a crystal face of the molecular sieve crystal grain as measured by a TEM-EDS method, and RE (C) represents the content of rare earth in any region of more than 100 nm² in an outward distance H from the geometric center of the crystal face of the molecular sieve crystal grain as measured by a TEM-EDS method, wherein H is 10% of the distance from a certain point on the edge of the crystal face to the geometric center of the crystal face.

In one embodiment, for the molecular sieve of MFI structure rich in mesopores, the molecular sieve of MFI structure has a ratio of $n(SiO_2)/n(Al_2O_3)$ of greater than 18 and less than 60; the molecular sieve has a content of phosphorus, calculated as $P_2O_5$, of 3-12 wt % based on the dry weight of the molecular sieve; the molecular sieve has a supported metal content, calculated as the oxide of the supported metal, of 3-8 wt % supported metal M1 and 0.5-3 wt % supported metal M2 based on the dry weight of the molecular sieve; and the volume of mesopores in the molecular sieve represents 45-65% by volume of the total pore volume of the molecular sieve.

In a second aspect, the present invention provides a process of producing the rare earth- and phosphorus-containing molecular sieve of MFI structure rich in mesopores of the first aspect, the process comprising:

a. filtering and washing a slurry of molecular sieve of MFI structure obtained by crystallization to provide a water-washed molecular sieve; wherein, the water-washed molecular sieve has a sodium content, calculated as sodium oxide, of less than 5 wt %, based on the total dry weight of the water-washed molecular sieve calculated as;

b. desiliconizing the water-washed molecular sieve obtained in step a in an alkaline solution, and then filtering and washing to provide a base washed molecular sieve;

c. carrying out an ammonium exchange treatment on the base washed molecular sieve obtained in step b to provide an ammonium exchanged molecular sieve; wherein the ammonium exchanged molecular sieve has a sodium content, calculated as sodium oxide, of less than 0.2 wt %, based on the total dry weight of the ammonium exchanged molecular sieve; and d. carrying out a phosphorus modification treatment, a supporting treatment with the supported metal and a baking treatment on the ammonium exchanged molecular sieve obtained in step c, to provide the rare earth- and phosphorus-containing molecular sieve of MFI structure rich in mesopores.

In one embodiment, for the process of producing the molecular sieve, wherein step d is carried out by one or more modes selected from the group consisting of:

mode (1): simultaneously carrying out a phosphorus modification treatment and a supporting treatment with the supported metal on the ammonium exchanged molecular sieve obtained in step c, and then carrying out the baking treatment;

mode (2): the supported metals M1 and M2 being respectively used for treatment, and the baking treatment comprising a baking treatment in a steam atmosphere and a baking treatment in an air atmosphere, wherein the ammonium exchanged molecular sieve obtained in step c is sequentially subjected to a supporting treatment with the supported metal M1, a baking treatment in a steam atmosphere, followed by a supporting treatment with the supported metal M2, a phosphorus modification treatment and a baking treatment in the air atmosphere;

mode (3): the supported metals M1 and M2 being respectively used for treatment, and sequentially carrying out a supporting treatment with the supported metal M1, followed by a supporting treatment with the supported metal M2, a phosphorus modification treatment and a baking treatment on the ammonium exchanged molecular sieve obtained in step c;

mode (4): the supported metals M1 and M2 being respectively used for treatment, and the baking treatment comprising a baking treatment in a steam atmosphere and a baking in an air atmosphere, wherein the ammonium exchanged molecular sieve obtained in step c is sequentially subjected to a phosphorus modification treatment, a supporting treatment with the supported metal M2 and a baking treatment in the air atmosphere, followed by a supporting treatment with the supported metal M1 and a baking treatment in a steam atmosphere.

In one embodiment, for the process of producing a molecular sieve, the molecular sieve of MFI structure in the slurry of molecular sieve of MFI structure obtained by crystallization is a ZSM-5 molecular sieve, having a silica-to-alumina ratio of less than 80.

In one embodiment, for the process of producing a molecular sieve, the slurry of the molecular sieve of MFI structure obtained by crystallization is prepared using a template method, and step b further comprises: carrying out drying and a baking on the water-washed molecular sieve to remove the template agent, followed by the desiliconization treatment.

In one embodiment, for the process of producing a molecular sieve, in step b, the alkaline solution is an aqueous solution of sodium hydroxide and/or in step b, potassium hydroxide; and/or the conditions for the desilication treatment comprise: a weight ratio of the molecular sieve calculated on a dry basis to the base and water in the alkaline solution of 1:(0.1-2):(5-15), a temperature of 10-100° C., preferably from room temperature to 100° C., and/or a treatment duration of 0.2-4 hours.

In one embodiment, for the process of producing a molecular sieve, in step c, the ammonium exchange treatment comprises treating the base washed molecular sieve with an aqueous solution of an ammonium salt, the ammonium exchange treatment conditions comprising: a weight ratio of the molecular sieve calculated on a dry basis to the ammonium salt and water of 1:(0.1-1):(5-10), a temperature of 10-100° C., preferably from room temperature to 100° C., and/or a treatment duration of 0.2-4 hours; and the ammonium salt is one or more selected from ammonium chloride, ammonium sulfate and ammonium nitrate.

In one embodiment, for the process of producing a molecular sieve, in step d, the phosphorus modification treatment comprises: carrying out impregnation and/or ion exchange with at least one phosphorus-containing compound selected from phosphoric acid, diammonium hydrogen phosphate, ammonium dihydrogen phosphate, and ammonium phosphate;

the supporting treatment with the supported metal comprises: supporting the supported metal in a single time or in batches by impregnation and/or ion exchange with a compound containing the supported metal; and the conditions for the baking treatment comprise: an atmosphere of air atmosphere and/or steam atmosphere, a baking temperature of 400-800° C., and/or a baking duration of 0.5-8 hours.

In a third aspect, the present invention provides a catalytic cracking catalyst, wherein the catalytic cracking catalyst comprises, based on the dry weight of the catalytic cracking catalyst:
- 5-75 wt % of the molecular sieve of MFI structure rich in mesopores of the first aspect;
- 0 to 30 wt % of a Y-type molecular sieve;
- 1-60 wt % of an inorganic binder comprising a phosphorus-aluminum inorganic binder and optionally an additional inorganic binder; and optionally
- 0 to 65 wt % of a second clay.

In one embodiment, the catalytic cracking catalyst comprises 2 to 45 wt %, preferably 3 to 39 wt %, on a dry basis of a phosphorus-aluminum inorganic binder and not more than 30 wt %, preferably 1 to 30 wt % on a dry basis of an additional inorganic binder, based on the dry weight of the catalytic cracking catalyst.

In one embodiment, for the catalytic cracking catalyst, the phosphorus-aluminum inorganic binder is an aluminophosphate gel and/or a first clay-containing phosphorus-aluminum inorganic binder; the first clay-containing phosphorus-aluminum inorganic binder comprises 15-40 wt %, of an aluminum component calculated as $Al_2O_3$, 45-80 wt %, of a phosphorus component calculated as $P_2O_5$, and more than 0 and not more than 40 wt %, of a first clay on dry basis, based on the dry weight of the first clay-containing phosphorus-aluminum inorganic binder, wherein the first clay-containing phosphorus-aluminum inorganic binder has a weight ratio of P/Al of 1.0-6.0, a pH value of 1-3.5, and a solid content of 15-60 wt %; the first clay comprises at least one of kaolin, sepiolite, attapulgite, rectorite, montmorillonite and diatomite; and the additional inorganic binder comprises at least one of pseudo-boehmite, alumina sol, silica-alumina sol and water glass.

In one embodiment, the catalytic cracking catalyst comprises the second clay, which is at least one selected from the group consisting of kaolin, sepiolite, attapulgite, rectorite, montmorillonite, halloysite, hydrotalcite, bentonite, and diatomaceous earth, preferably at least one selected from the group consisting of kaolin, metakaolin, diatomaceous earth, sepiolite, attapulgite, montmorillonite, and rectorite.

In one embodiment, the catalytic cracking catalyst of the third aspect of the invention is a I-type catalytic cracking catalyst, characterized in that the I-type catalytic cracking catalyst comprises:
- 10-75 wt % of a rare earth- and phosphorus-containing molecular sieve of MFI structure rich in mesopores;
- 1-40 wt % of a binder; and
- 0 to 65 wt %, preferably 5 to 55 wt %, of a second clay.

In a particular embodiment, the I-type catalytic cracking catalyst may be used alone as the catalytic cracking catalyst in a catalytic cracking reactor. In another particular embodiment, a mixture of the I-type catalytic cracking catalyst and an additional conventional catalytic cracking catalyst may be used as a catalytic cracking catalyst in a catalytic cracking reactor. In the case of a mixture used, the I-type catalytic cracking catalyst of the present invention may be used in an amount of not more than 30 wt %, preferably 1 to 25 wt %, more preferably 3 to 15 wt %, based on the total amount of the mixture.

In one embodiment, the catalytic cracking catalyst of the third aspect of the present invention is a II-type catalytic cracking catalyst, wherein the II-type catalytic cracking catalyst comprises, based on the dry weight of the catalytic cracking catalyst:
- 5-55 wt % of a molecular sieve of MFI structure rich in mesopores;
- 1 to 60 wt % of an inorganic binder;
- 1-30 wt % of a Y-type molecular sieve; and optionally
- 0 to 60 wt % of the second clay.

In the present application, when a "catalytic cracking catalyst" is mentioned, it is to be understood as referring to any catalytic cracking catalyst according to the third aspect of the invention, including the I-type and/or II-type catalytic cracking catalysts, unless specified as applicable to the I-type and/or II-type catalytic cracking catalyst or other catalytic cracking catalysts.

In one embodiment, the catalytic cracking catalyst is characterized in that the Y-type molecular sieve comprises at least one of PSRY molecular sieve, PSRY-S molecular sieve, rare earth-containing PSRY molecular sieve, rare earth-containing PSRY-S molecular sieve, USY molecular sieve, rare earth-containing USY molecular sieve, REY molecular sieve, REHY molecular sieve, and HY molecular sieve.

In a fourth aspect, the present invention provides a process of producing a catalytic cracking catalyst as described in the third aspect, comprising:
- mixing the rare earth- and phosphorus-containing molecular sieve of MFI structure rich in mesopores as described in the first aspect with an inorganic binder and optionally a second clay, to produce a slurry;
- spray drying the slurry; and optionally
- carrying out a third baking treatment;
- wherein, relative to 5 to 75 parts by weight of the rare earth- and phosphorus-containing molecular sieve of MFI structure rich in mesopores on a dry basis, the amount of the inorganic binder on a dry basis is 1 to 60 parts by weight, and the amount of the second clay on a dry basis is 0 to 65 parts by weight; and
- wherein the binder comprises a phosphorus-aluminum inorganic binder and optionally an additional inorganic binder.

In one embodiment, for the process of producing a catalytic cracking catalyst, the process comprises the third baking, and further comprises: washing and optionally drying the product obtained from the third baking; wherein the third baking is carried out at a baking temperature of 300-650° C. for 0.5-12 h, preferably 0.5-8 h; and the drying is carried out at a temperature of 100-200° C. for 0.5-24 h.

In one embodiment, for the process of producing a catalytic cracking catalyst, the phosphorus-aluminum inorganic binder comprises a first clay-containing phosphorus-aluminum inorganic binder, and the process further comprises: preparing the first clay-containing phosphorus-aluminum inorganic binder by the steps of:
- formulating an alumina source, the first clay and water into a slurry with a solid content of 5-48 wt %; wherein the alumina source is aluminum hydroxide and/or alumina capable of being peptized by an acid, and the first clay is used in an amount of more than 0 part by weight and not more than 40 parts by weight on a dry basis, relative to 15-40 parts by weight of the alumina source calculated as $Al_2O_3$; and
- adding concentrated phosphoric acid into the slurry at a weight ratio of P/Al=1-6 under stirring, and reacting the mixed slurry at 50-99° C. for 15-90 minutes; wherein the P in the P/Al represents the weight of phosphorus in the phosphoric acid calculated as a simple substance, and Al represents the weight of aluminum in the alumina source calculated as a simple substance.

In one embodiment, for the process of producing a catalytic cracking catalyst, the Y-type molecular sieves are further added and mixed before the slurry is prepared.

In a fifth aspect, the present invention provides a method for catalytically cracking a hydrocarbon oil using the catalytic cracking catalyst of the third aspect, comprising: contacting and reacting the hydrocarbon oil with the catalytic cracking catalyst under the catalytic cracking reaction condition, wherein the catalytic cracking reaction is carried out at a temperature of 500-800° C.

In one embodiment, regarding the method for catalytically cracking a hydrocarbon oil, the hydrocarbon oil is one or more selected from crude oil, naphtha, gasoline, atmospheric residue, vacuum residue, atmospheric wax oil, vacuum wax oil, straight-run wax oil, propane light/heavy deoiling, coked wax oil, and coal liquefaction product.

In one embodiment, regarding the method for catalytically cracking a hydrocarbon oil, the hydrocarbon oil is contacted and reacted with a catalytic mixture containing the catalytic cracking catalyst of the present invention and an additional conventional catalytic cracking catalyst.

In one embodiment, regarding the method for catalytically cracking a hydrocarbon oil, the content of the catalytic cracking catalyst according to the present invention in the catalytic mixture is 0.1 to 30 wt %.

For example, the present invention provides the following four series of exemplary schemes:

A first series of exemplary schemes comprise, but not limited to:

1. An exemplary scheme 1 of the first series according to the present invention provides a rare earth- and phosphorus-containing molecular sieve of MFI structure rich in mesopores, which molecular sieve has a ratio of n(SiO$_2$)/n(Al$_2$O$_3$) of more than 15 and less than 70; the molecular sieve has a content of phosphorus, calculated as P$_2$O$_5$, of 1-15 wt % based on the dry weight of the molecular sieve; the molecular sieve has a supported metal content, calculated as the oxide of the supported metal, of 1-10 wt % supported metal M1 and 0.1-5 wt % supported metal M2 based on the dry weight of the molecular sieve, wherein the supported metal M1 is one or two selected from lanthanum and cerium, and the supported metal M2 is one selected from iron, cobalt, nickel, copper, manganese, zinc, tin, bismuth and gallium; and the volume of mesopores in the molecular sieve represents 40-70% by volume of the total pore volume of the molecular sieve, wherein the volume of mesopores and the total pore volume of the molecular sieve are measured by a nitrogen adsorption BET specific surface area method, and the volume of mesopores means the pore volume of the pores having a diameter of more than 2 nm and less than 100 nm.

2. The molecular sieve of MFI structure of the exemplary scheme 1 of the first series, wherein the molecular sieve has a ratio of n(SiO$_2$)/n(Al$_2$O$_3$) of greater than 18 and less than 60; the molecular sieve has a content of phosphorus, calculated as P$_2$O$_5$, of 3-12 wt % based on the dry weight of the molecular sieve; the molecular sieve has a supported metal content, calculated as the oxide of the supported metal, of 3-8 wt % supported metal M1 and 0.5-3 wt % supported metal M2 based on the dry weight of the molecular sieve; and the volume of mesopores in the molecular sieve represents 45-65% by volume of the total pore volume of the molecular sieve.

3. An exemplary scheme 3 of the first series according to the present invention provides a process of producing a rare earth- and phosphorus-containing molecular sieve of MFI structure rich in mesopores as set forth in exemplary scheme 1 or 2 of the first series, the process comprising:

a. filtering and washing the slurry of the molecular sieve of MFI structure obtained by crystallization to provide a water-washed molecular sieve; wherein, the water-washed molecular sieve has a sodium content, calculated as sodium oxide, of less than 5 wt % based on the total dry weight of the water-washed molecular sieve calculated as sodium oxide;

b. desiliconizing the water-washed molecular sieve obtained in step a in an alkaline solution, and filtering and washing to provide a base washed molecular sieve;

c. carrying out ammonium exchange treatment on the base washed molecular sieve obtained in step b to provide an ammonium exchanged molecular sieve; wherein the ammonium exchanged molecular sieve has a sodium content, calculated as sodium oxide, of less than 0.2 wt %, based on the total dry weight of the ammonium exchanged molecular sieve;

d. carrying out phosphorus modification treatment, supporting treatment with the supported metal and baking treatment on the ammonium exchanged molecular sieve obtained in step c, to provide the rare earth- and phosphorus-containing molecular sieve of MFI structure rich in mesopores.

4. The process according to the exemplary scheme 3 of the first series, wherein the molecular sieve of MFI structure in the slurry of the molecular sieve of MFI structure obtained by crystallization is a ZSM-5 molecular sieve, having a silica-to-alumina ratio of less than 80.

5. The process according to the exemplary scheme 3 of the first series, wherein, if the slurry of the molecular sieve of MFI structure obtained by crystallization is prepared by a template method, then step b further comprises: drying and baking the water-washed molecular sieve to remove the template agent, and then carrying out the desiliconization treatment.

6. The process according to the exemplary scheme 3 of the first series, wherein in step b, the base in the alkaline solution is sodium hydroxide and/or potassium hydroxide.

7. The process according to the exemplary scheme 3 of the first series, wherein in step b, the conditions for the desilication treatment comprise: a weight ratio of the molecular sieve calculated on a dry basis to the base and water in the alkaline solution of 1:(0.1-2):(5-15), a temperature of from room temperature to 100° C., and a duration of 0.2-4 hours.

8. The process according to the exemplary scheme 3 of the first series, wherein in step c, the ammonium exchange treatment conditions comprise: a weight ratio of the molecular sieve calculated on a dry basis to the ammonium salt and water is 1:(0.1-1):(5-10), a temperature of from room temperature to 100° C., and a duration of 0.2-4 hours.

9. The process according to the exemplary scheme 8 of the first series, wherein the ammonium salt is one or more selected from ammonium chloride, ammonium sulfate, and ammonium nitrate.

10. The process according to the exemplary scheme 3 of the first series, wherein in step d, the phosphorus modification treatment comprises: carrying out impregnation and/or ion-exchange to the molecular sieve with at least one phosphorus-containing compound selected from the group consisting of phosphoric acid, diammonium hydrogen phosphate, ammonium dihydrogen phosphate, and ammonium phosphate.

11. The process according to the exemplary scheme 3 of the first series, wherein in step d, the supporting treatment with the supported metal comprises: supporting a compound containing a supported metal onto the molecular sieve by impregnation and/or ion exchange in a single time or in batches.

12. The process according to the exemplary scheme 3 of the first series, wherein in step d, the conditions for the baking treatment comprise: an atmosphere of air atmosphere and/or steam atmosphere, a baking temperature of 400-800° C., and a baking duration of 0.5-8 hours.

A second series of exemplary schemes comprise, but not limited to:

1. An exemplary scheme 1 according to the second series of the present invention provides a rare earth- and phosphorus-containing molecular sieve of MFI structure rich in mesopores, which has a ratio of $n(SiO_2)/n(Al_2O_3)$ of more than 15 and less than 70; the molecular sieve has a content of phosphorus, calculated as $P_2O_5$, of 1-15 wt % based on the dry weight of the molecular sieve; the molecular sieve has a supported metal content, calculated as the oxide of the supported metal, of 1-10 wt % supported metal M1 and 0.1-5 wt % supported metal M2 based on the dry weight of the molecular sieve, wherein the supported metal M1 is one or two selected from lanthanum and cerium, and the supported metal M2 is one selected from iron, cobalt, nickel, copper, manganese, zinc, tin, bismuth and gallium; and the volume of mesopores in the molecular sieve represents 40-70% by volume of the total pore volume of the molecular sieve, wherein the volume of mesopores and the total pore volume of the molecular sieve is measured by a nitrogen adsorption BET specific surface area method, and the volume of mesopores refers to the pore volume of the pores having a diameter of more than 2 nm and less than 100 nm.

2. The molecular sieve of MFI structure according to the exemplary scheme 1 of the second series, wherein the molecular sieve has a RE distribution parameter, D, satisfying: $0.9 \leq D \leq 1.1$, wherein D=RE (S)/RE (C), RE (S) represents the content of the rare earth in any region of more than 100 $nm^2$ within an inward distance of H from the edge of a crystal face of the molecular sieve crystal grain measured by a TEM-EDS method, and RE (C) represents the content of rare earth in any region of more than 100 $nm^2$ in an outward distance H from the geometric center of the crystal face of the molecular sieve crystal grain measured by a TEM-EDS method, and H is 10% of the distance from a certain point of the edge of the crystal face to the geometric center of the crystal face.

3. The molecular sieve of MFI structure according to the exemplary scheme 1 or 2 of the second series, wherein the molecular sieve has a ratio of $n(SiO_2)/n(Al_2O_3)$ of greater than 18 and less than 60; the molecular sieve has a content of phosphorus, calculated as $P_2O_5$, of 3-12 wt % based on the dry weight of the molecular sieve; the molecular sieve has a supported metal content, calculated as the oxide of the supported metal, of 3-8 wt % supported metal M1 and 0.5-3 wt % supported metal M2 based on the dry weight of the molecular sieve; and the volume of mesopores in the molecular sieve represents 45-65% by volume of the total pore volume of the molecular sieve.

4. The exemplary scheme 4 of the second series of the present invention provides a process of producing a rare earth- and phosphorus-containing molecular sieve of MFI structure rich in mesopores, which comprises:
   a. filtering and washing a slurry of the molecular sieve of MFI structure obtained by crystallization to provide a water-washed molecular sieve; wherein, the water-washed molecular sieve has a sodium content, calculated as sodium oxide, of less than 5 wt % based on the total dry weight of the water-washed molecular sieve calculated as sodium oxide;
   b. desiliconizing the water-washed molecular sieve obtained in step a in an alkaline solution, and filtering and washing to provide a base washed molecular sieve;
   c. carrying out ammonium exchange treatment on the base washed molecular sieve obtained in step b to provide an ammonium exchanged molecular sieve; wherein the ammonium exchanged molecular sieve has a sodium content, calculated as sodium oxide, of less than 0.2 wt %, based on the total dry weight of the ammonium exchanged molecular sieve;
   d. carrying out phosphorus modification treatment, supporting treatment with the supported metal and baking treatment on the ammonium exchanged molecular sieve obtained in step c to provide the rare earth- and phosphorus-containing molecular sieve of MFI structure rich in mesopores.

5. The process according to the exemplary scheme 4 of the second series, wherein step d is one or more selected from the following modes:
   mode (1): simultaneously carrying out a phosphorus modification treatment and the supporting treatment with the supported metal on the ammonium exchanged molecular sieve obtained in step c, and then carrying out the baking treatment;
   mode (2): sequentially carrying out the supporting treatment with the supported metal M1, baking treatment in a steam atmosphere, followed by a supporting treatment with the supported metal M2, phosphorus modification treatment and baking treatment in an air atmosphere on the ammonium exchanged molecular sieve obtained in step c;
   mode (3): sequentially carrying out the supporting treatment with the supported metal M1, followed by a supporting treatment with the supported metal M2, phosphorus modification treatment and baking treatment on the ammonium exchanged molecular sieve obtained in step c; and
   mode (4): sequentially carrying out a phosphorus modification treatment, fa supporting treatment with the supported metal M2, the baking treatment in an air atmosphere, followed by the supporting treatment with the supported metal M1 and the baking treatment in a steam atmosphere on the ammonium exchanged molecular sieve obtained in step c.

6. The process according to the exemplary scheme 4 or 5 of the second series, wherein the molecular sieve of MFI structure in the slurry of the molecular sieve of MFI structure obtained by crystallization is a ZSM-5 molecular sieve, having a silica-to-alumina ratio of less than 80.

7. The process according to the exemplary scheme 4 or 5 of the second series, wherein, if the slurry of the molecular sieve of MFI structure obtained by crystallization is prepared by a template method, then step b further comprises: drying and baking the water-washed molecular sieve to remove the template agent, and then carrying out the desiliconization treatment.

8. The process according to the exemplary scheme 4 or 5 of the second series, wherein in step b, the base in the alkaline solution is sodium hydroxide and/or potassium hydroxide; and
   in step b, the conditions for the desiliconization treatment comprise: a weight ratio of the molecular sieve calculated on a dry basis to the base and water in the alkaline solution of 1:(0.1-2):(5-15), a temperature of from room temperature to 100° C., and a duration of 0.2-4 hours.

9. The process according to the exemplary scheme 4 or 5 of the second series, wherein in step c, the conditions for the ammonium exchange treatment comprise: a weight ratio on a dry basis of the molecular sieve to the ammonium salt and water of 1:(0.1-1):(5-10), a temperature of from room temperature to 100° C., and a duration of 0.2-4 hours;

the ammonium salt is one or more selected from ammonium chloride, ammonium sulfate and ammonium nitrate.

10. The process according to the exemplary scheme 4 or 5 of the second series, wherein in step d, the phosphorus modification treatment comprises: carrying out impregnation and/or ion-exchange to the molecular sieve with at least one phosphorus-containing compound selected from phosphoric acid, diammonium hydrogen phosphate, ammonium dihydrogen phosphate and ammonium phosphate;

the supporting treatment with the supported metal comprises: supporting a compound containing a supported metal onto the molecular sieve by impregnation and/or ion exchange in a single time or in batches; and the conditions for the baking treatment comprise: an atmosphere of air atmosphere and/or steam atmosphere, a baking temperature of 400-800° C., and a baking duration of 0.5-8 hours.

A third series of exemplary schemes comprise, but not limited to:

1. An exemplary scheme 1 of the third series according to the present invention provides a catalytic cracking catalyst, characterized in that the catalytic cracking catalyst comprises 1 to 30 wt %, on a dry basis, of Y-type molecular sieve, 5 to 55 wt %, on a dry basis, of a phosphorus- and metal-containing molecular sieve of MFI structure rich in mesopores, 1 to 60 wt % of inorganic binder, and optionally 0 to 60 wt % of second clay, wherein the inorganic binder comprises phosphor-aluminum inorganic binder and/or an additional inorganic binder;

wherein the phosphorus- and metal-containing molecular sieve of MFI structure rich in mesopores has a ratio of $n(SiO_2)/n(Al_2O_3)$ of more than 15 and less than 70; the molecular sieve has a content of phosphorus, calculated as $P_2O_5$, of 1-15 wt % based on the dry weight of the phosphorus- and metal-containing molecular sieve of MFI structure rich in mesopores; the phosphorus- and metal-containing molecular sieve of MFI structure rich in mesopores has a content of the supported metal, calculated as the oxide of the supported metal, of 1-10 wt % supported metal M1 and 0.1-5 wt % supported metal M2, based on the dry weight of the phosphorus- and metal-containing molecular sieve of MFI structure rich in mesopores, wherein the supported metal M1 is one or two selected from lanthanum and cerium, and the supported metal M2 is one selected from iron, cobalt, nickel, copper, manganese, zinc, tin, bismuth and gallium; and the volume of mesopores in the molecular sieve represents 40-70% by volume of the total pore volume of the phosphorus- and metal-containing molecular sieve of MFI structure rich in mesopores, wherein the volume of mesopores and the total pore volume of the phosphorus- and metal-containing molecular sieve of MFI structure rich in mesopores are measured by a nitrogen adsorption BET specific surface area method, and the volume of mesopores means the pore volume of the pores having a diameter of greater than 2 nm and less than 100 nm.

2. The catalytic cracking catalyst according to the exemplary scheme 1 of the third series, wherein the phosphorus- and metal-containing molecular sieve rich in mesopores has a RE distribution parameter, D, satisfying: $0.9 \leq D \leq 1.3$, wherein D=RE (S)/RE (C), RE (S) represents the content of the rare earth in any region of more than 100 $nm^2$ within an inward distance of H from the edge of a crystal face of the molecular sieve crystal grain measured by a TEM-EDS method, and RE (C) represents the content of rare earth in any region of more than 100 $nm^2$ in an outward distance H from the geometric center of the crystal face of the molecular sieve crystal grain measured by a TEM-EDS method, and H is 10% of the distance from a certain point of the edge of the crystal face to the geometric center of the crystal face.

3. The catalytic cracking catalyst of the exemplary scheme 1 or 2 of the third series, wherein the phosphorus- and metal-containing molecular sieve of MFI structure rich in mesopores has a ratio of $n(SiO_2)/n(Al_2O_3)$ of greater than 18 and less than 60; the molecular sieve has a content of phosphorus, calculated as $P_2O_5$, of 3-12 wt % based on the dry weight of the phosphorus- and metal-containing molecular sieve of MFI structure rich in mesopores; the molecular sieve has a content of the supported metal, calculated as the oxide of the supported metal, of 3-8 wt % supported metal M1 and 0.5-3 wt % supported metal M2, based on the dry weight of the phosphorus- and metal-containing molecular sieve of MFI structure rich in mesopores; and the volume of mesopores in the molecular sieve represents 45-65% by volume of the total pore volume of the phosphorus- and metal-containing molecular sieve of MFI structure rich in mesopores.

4. The catalytic cracking catalyst according to the exemplary scheme 1 of the third series, wherein the catalytic cracking catalyst comprises 2 to 45 wt % on a dry basis of the phosphorus-aluminum inorganic binder and/or not more than 30 wt % on a dry basis of an additional inorganic binder, based on the dry weight of the catalytic cracking catalyst.

5. The catalytic cracking catalyst of the exemplary scheme 4 of the third series, wherein the phosphorus-aluminum inorganic binder is an aluminophosphate gel and/or a first clay-containing phosphorus-aluminum inorganic binder; the first clay-containing phosphorus-aluminum inorganic binder comprises 15-40 wt % of an aluminum component calculated as $Al_2O_3$, 45-80 wt % of a phosphorus component calculated as $P_2O_5$ and more than 0 and not more than 40 wt % of the first clay on a dry basis, wherein the first clay-containing phosphorus-aluminum inorganic binder has a weight ratio of P/Al of 1.0-6.0, a pH value of 1-3.5, and a solid content of 15-60 wt %; and the first clay comprises at least one of kaolin, sepiolite, attapulgite, rectorite, montmorillonite and diatomite; and the additional inorganic binder comprises at least one of pseudo-boehmite, alumina sol, silica-alumina sol and water glass.

6. The catalytic cracking catalyst of the exemplary scheme 1 of the third series, wherein the second clay is at least one selected from kaolin, metakaolin, diatomaceous earth, sepiolite, attapulgite, montmorillonite and rectorite.

7. The catalytic cracking catalyst of the exemplary scheme 1 of the third series, wherein the Y-type molecular sieve comprises at least one of a PSRY molecular sieve, a PSRY-S molecular sieve, a Rare earth-containing PSRY molecular sieve, a Rare earth-containing PSRY-S molecular sieve, a USY molecular sieve, a Rare earth-containing USY molecular sieve, a REY molecular sieve, a REHY molecular sieve and an HY molecular sieve.

8. An exemplary scheme 8 of the third series of the present invention provides a process of producing a catalytic cracking catalyst, comprising: mixing a Y-type molecular sieve, a phosphorus- and metal-containing molecular sieve of MFI structure rich in mesopores and an inorganic binder for formulating slurry, spray-drying, and optionally baking to provide the catalytic cracking catalyst; wherein a second clay is added or not added to the mixing; and on a dry basis, the Y-type molecular sieve, the phosphorus- and metal-containing molecular sieve of MFI structure rich in mesopores, the inorganic binder and the second clay are used at a ratio by weight of (1-30):(5-55):(1-60):(0 to 60);

the inorganic binder comprises a phosphorus-aluminum inorganic binder and/or an additional inorganic binder; the phosphorus- and metal-containing molecular sieve of MFI structure rich in mesopores has a ratio of $n(SiO_2)/n(Al_2O_3)$ of more than 15 and less than 70; the phosphorus- and metal-containing molecular sieve of MFI structure rich in mesopores has a content of phosphorus, calculated as $P_2O_5$, of 1-15 wt % based on the dry weight of the molecular sieve; the phosphorus- and metal-containing molecular sieve of MFI structure rich in mesopores has a content, on a dry basis, of the supported metal of 1-10 wt % supported metal M1 and 0.1-5 wt % supported metal M2, wherein the supported metal M1 is one or two selected from lanthanum and cerium, and the supported metal M2 is one selected from iron, cobalt, nickel, copper, manganese, zinc, tin, bismuth and gallium; and the volume of mesopores in the molecular sieve represents 40-70% by volume of the total pore volume of the molecular sieve, wherein the volume of mesopores and the total pore volume of the molecular sieve are measured by a nitrogen adsorption BET specific surface area method, and the volume of mesopores means the pore volume of the pores having a diameter greater than 2 nm and less than 100 nm.

9. The process according to the exemplary scheme 8 of the third series, wherein the process further comprises: washing and optionally drying the product obtained from baking to provide the catalytic cracking catalyst; wherein the first baking treatment is carried out at a baking temperature of 300-650° C., and a baking duration of 0.5-12 h.

10. The process of exemplary scheme 8 of the third series, wherein the Y-type molecular sieve comprises at least one of a PSRY molecular sieve, a PSRY-S molecular sieve, a rare earth-containing PSRY molecular sieve, a rare earth-containing PSRY-S molecular sieve, a USY molecular sieve, a rare earth-containing USY molecular sieve, a REY molecular sieve, a REHY molecular sieve, and an HY molecular sieve; the second clay is at least one selected from kaolin, metakaolin, diatomite, sepiolite, attapulgite, montmorillonite and rectorite.

11. The process of exemplary scheme 8 of the third series, wherein the binder comprises the phosphorus-aluminum inorganic binder and the additional inorganic binders; and relative to 1 to 30 parts by weight on a dry basis of the Y-type molecular sieve, the phosphorus-aluminum inorganic binder is used in an amount of 2 to 45 parts by weight on a dry basis, and the additional inorganic binder is used in an amount of 1 to 30 parts by weight on a dry basis; wherein the additional inorganic binder comprises at least one of pseudo-boehmite, alumina sol, silica-alumina sol and water glass; and the phosphorus-aluminum inorganic binder is aluminophosphate gel and/or a first clay-containing phosphorus-aluminum inorganic binder containing.

12. The process according to the exemplary scheme 11 of the third series, wherein the process further comprises: preparing the first clay-containing phosphorus-aluminum inorganic binder by the steps of:

formulating an alumina source, the first clay and water into a slurry, and dispersing the slurry to have a solid content of 5-48 wt %; wherein the alumina source is aluminum hydroxide and/or alumina capable of being peptized by an acid, and the amount of the first clay, on a dry basis, is more than 0 part by weight and not more than 40 part by weight relative to 15-40 part by weight of the alumina source calculated as $Al_2O_3$;

adding concentrated phosphoric acid into the slurry at a weight ratio of P/Al=1-6 under stirring, and reacting the mixed slurry for 15-90 minutes at 50-99° C.; wherein in the P/Al, P is the weight of phosphorus in the phosphoric acid calculated as a simple substance, and Al is the weight of aluminum in the alumina source calculated as a simple substance.

13. The process according to the exemplary scheme 8 of the third series, wherein the process further comprises: producing the phosphorus- and metal-containing molecular sieve of MFI structure rich in mesopores by the steps of:

a. filtering and washing a slurry of the molecular sieve of MFI structure obtained by crystallization to provide a water-washed molecular sieve; wherein, the water-washed molecular sieve has a sodium content, calculated as sodium oxide, of less than 5 wt % based on the total dry weight of the water-washed molecular sieve;

b. desiliconizing the water-washed molecular sieve obtained in step a in an alkaline solution, and filtering and washing to provide a base washed molecular sieve;

c. carrying out ammonium exchange treatment on the base washed molecular sieve obtained in step b to provide an ammonium exchanged molecular sieve; wherein the ammonium exchanged molecular sieve has a sodium content, calculated as sodium oxide, of less than 0.2 wt %, based on the total dry weight of the ammonium exchanged molecular sieve;

d. carrying out phosphorus modification treatment, supporting treatment with the supported metal and a third baking treatment on the ammonium exchanged molecular sieve obtained in step c to provide the phosphorus- and metal-containing molecular sieve of MFI structure rich in mesopores.

14. The process according to the exemplary scheme 13 of the third series, wherein step d is one or more selected from the modes of:

mode (1): simultaneously carrying out a phosphorus modification treatment and a supporting treatment with the supported metal on the ammonium exchanged molecular sieve obtained in step c, and then carrying out the third baking treatment;

mode (2): sequentially carrying out supporting treatment with the supported metal M1, a third baking treatment in a steam atmosphere, followed by a supporting treatment with the supported metal M2, a phosphorus modification treatment and a third baking treatment in an air atmosphere on the ammonium exchanged molecular sieve obtained in step c;

mode (3): sequentially carrying out supporting treatment with the supported metal M1, followed by a supporting treatment with the supported metal M2, a phosphorus modification treatment and a third baking treatment on the ammonium exchanged molecular sieve obtained in step c; and mode (4): sequentially carrying out a phosphorus modification treatment, a supporting treatment with the supported metal M2, a third baking treatment in an air atmosphere, followed by a supporting treatment with the supported metal M1 and a third baking treatment in a steam atmosphere on the ammonium exchanged molecular sieve obtained in step c.

15. The process according to the exemplary scheme 13 of the third series, wherein the molecular sieve of MFI structure in the slurry of the molecular sieve of MFI structure obtained by crystallization is a ZSM-5 molecular sieve, having a silica-to-alumina ratio of less than 80; and if the slurry of the molecular sieve of MFI structure obtained by crystallization is prepared by a template method, step b further comprises: drying the water-washed molecular sieve and carrying out a fourth baking to remove the template agent, and then carrying out desiliconization treatment.

16. The process according to the exemplary scheme 13 of the third series, wherein in step b, the base in the alkaline solution is sodium hydroxide and/or potassium hydroxide;

the conditions for the desiliconization treatment comprise: a weight ratio of the molecular sieve calculated on a dry basis to the base and water in the alkaline solution of 1:(0.1-2):(5-15), a temperature of 10-100° C. and a duration of 0.2-4 hours.

17. The process according to the exemplary scheme 13 or 14 of the third series, wherein in step c, the conditions for the ammonium exchange treatment comprise: a weight ratio on a dry basis of the molecular sieve to the ammonium salt and water of 1:(0.1-1):(5-10), a temperature of 10-100° C., and a duration of 0.2-4 hours;

the ammonium salt is one or more selected from ammonium chloride, ammonium sulfate and ammonium nitrate.

18. The process according to the exemplary scheme 13 or 14 of the third series, wherein in step d, the phosphorus modification treatment comprises: carrying out impregnation and/or ion-exchange to the molecular sieve with at least one phosphorus-containing compound selected from phosphoric acid, diammonium hydrogen phosphate, ammonium dihydrogen phosphate and ammonium phosphate;

the supporting treatment with the supported metal comprises: supporting a compound containing the supported metal onto the molecular sieve by impregnation and/or ion exchange in a single time or in batches;

the conditions for the third baking treatment comprise: an atmosphere of air atmosphere and/or steam atmosphere, a baking temperature of 400-800° C., and a baking duration of 0.5-8 hours.

19. A catalytic cracking catalyst produced by the process according to any one of the exemplary schemes 8 to 18 of the third series.

20. An exemplary scheme 20 of the third series according to the present invention provides a method for catalytically cracking hydrocarbon oil, characterized in that the method comprises: contacting and reacting the hydrocarbon oil with the catalytic cracking catalyst described in any one of the exemplary schemes 1 to 7 of the third series and the exemplary scheme 19 of the third series under catalytic cracking reaction conditions.

21. The method according to the exemplary scheme 20 of the third series, wherein the catalytic cracking reaction conditions comprise: a reaction temperature of 500-800° C.; and the hydrocarbon oil is one or more selected from crude oil, naphtha, gasoline, atmospheric residue, vacuum residue, atmospheric wax oil, vacuum wax oil, straight-run wax oil, propane light/heavy deoiling, coked wax oil, and coal liquefaction product.

A fourth series of exemplary schemes comprise, but not limited to:

1. An exemplary scheme 1 of the fourth series according to the present invention provides a catalytic cracking aid, characterized in that the catalytic cracking aid comprises 10 to 75 wt % of a phosphorus- and rare earth-containing molecular sieve of MFI structure rich in mesoporous rich in mesoporous based on a dry weight of the catalytic cracking aid, 1 to 40 wt % of a binder based on the dry weight, and 0 to 65 wt % of a second clay based on the dry weight; wherein the binder comprises a phosphor-aluminum inorganic binder and/or an additional inorganic binder;

the rare earth- and phosphorus-containing molecular sieve of MFI structure rich in mesopores has a ratio of $n(SiO_2)/n(Al_2O_3)$ of more than 15 and less than 70; the molecular sieve has a phosphorus content, calculated as $P_2O_5$, of 1-15 wt % based on the dry weight of the molecular sieve; the molecular sieve has a supported metal content, calculated as the oxide of the supported metal, of 1-10 wt % supported metal M1 and 0.1-5 wt % supported metal M2 based on the dry weight of the molecular sieve, wherein the supported metal M1 is one or two selected from lanthanum and cerium, and the supported metal M2 is one selected from iron, cobalt, nickel, copper, manganese, zinc, tin, bismuth and gallium; and the volume of mesopores in the molecular sieve represents 40-70% by volume of the total pore volume of the molecular sieve, wherein the volume of mesopores and the total pore volume of the molecular sieve are measured by a nitrogen adsorption BET specific surface area method, and the volume of mesopores means the pore volume of the pores having a diameter of more than 2 nm and less than 100 nm.

2. The catalytic cracking aid according to the exemplary scheme 1 of the fourth series, wherein the molecular sieve has an RE distribution parameter, D, satisfying: $0.9 \leq D \leq 1.3$, wherein D=RE (S)/RE (C), RE (S) represents the content of the rare earth in any region of more than 100 nm$^2$ within an inward distance of H from the edge of a crystal face of the molecular sieve crystal grain measured by a TEM-EDS method, RE (C) represents the content of rare earth in any region of more than 100 nm$^2$ in an outward distance H from the geometric center of the crystal face of the molecular sieve crystal grain measured by a TEM-EDS method, and H is 10% of the distance from a certain point of the edge of the crystal face to the geometric center of the crystal face.

3. The catalytic cracking aid according to the exemplary scheme 1 or 2 of the fourth series, wherein the molecular sieve has a ratio of $n(SiO_2)/n(Al_2O_3)$ of more than 18 and less than 60; the molecular sieve has a content of phosphorus, calculated as $P_2O_5$, of 3-12 wt % based on the dry weight of the molecular sieve; the molecular sieve has a supported metal content, calculated as the oxide of the supported metal, of 3-8 wt % supported metal M1 and 0.5-3 wt % supported metal M2 based on the dry weight of the molecular sieve; and the volume of mesopores in the molecular sieve represents 45-65% by volume of the total pore volume of the molecular sieve 45-65%.

4. The catalytic cracking aid according to the exemplary scheme 1 of the fourth series, wherein the phosphorus-aluminum inorganic binder is an aluminophosphate gel and/or a first clay-containing phosphorus-aluminum inorganic binder; the first clay-containing phosphorus-aluminum inorganic binder comprises 15-40 wt % of an aluminum component calculated as $Al_2O_3$, 45-80 wt % of a phosphorus component calculated as $P_2O_5$ and more than 0 and not more than 40 wt % of the first clay on a dry basis, wherein the first clay-containing phosphorus-aluminum inorganic binder has a weight ratio of P/Al of 1.0-6.0, a pH value of 1-3.5, and a solid content of 15-60 wt %; and the first clay comprises at least one of kaolin, sepiolite, attapulgite, rectorite, montmorillonite and diatomite; and the additional inorganic binder comprises at least one of pseudo-boehmite, alumina sol, silica-alumina sol and water glass.

5. The catalytic cracking aid according to the exemplary scheme 1 of the fourth series, wherein the second clay is at least one selected from kaolin, sepiolite, attapulgite, rectorite, montmorillonite, halloysite, hydrotalcite, bentonite, and diatomaceous earth.

6. The catalytic cracking aid according to the exemplary scheme 1 of the fourth series, wherein the binder comprises 3 to 39 wt % on a dry basis of the phosphorus-aluminum inorganic binder and 1 to 30 wt % on a dry basis of the additional inorganic binder, based on a total weight of the catalytic cracking aid.

7. An exemplary scheme of the fourth series 7 of the present invention provides a process of producing a catalytic cracking aid, comprising: mixing the rare earth- and phosphorus-containing molecular sieve of MFI structure rich in mesopores, a binder and optionally a second clay for formulating slurry, and carrying out spray drying to provide the catalytic cracking aid; wherein the binder is used in an amount of 1 to 40 parts by weight on a dry basis, and the second clay is used in an amount of 0 to 65 parts by weight on a dry basis, relative to 10 to 75 parts by weight of the rare earth- and phosphorus-containing molecular sieve of MFI structure rich in mesoporous on a dry basis;

wherein the binder comprises a phosphor-aluminum inorganic binder and/or an additional inorganic binder; the rare earth- and phosphorus-containing molecular sieve of MFI structure rich in mesopores has a ratio of $n(SiO_2)/n(Al_2O_3)$ of more than 15 and less than 70; the molecular sieve has a content of phosphorus, calculated as $P_2O_5$, of 1-15 wt % based on the dry weight of the molecular sieve; the molecular sieve has a supported metal content, calculated as the oxide of the supported metal, of 1-10 wt % supported metal M1 and 0.1-5 wt % supported metal M2 based on the dry weight of the molecular sieve, wherein the supported metal M1 is one or two selected from lanthanum and cerium, and the supported metal M2 is one selected from iron, cobalt, nickel, copper, manganese, zinc, tin, bismuth and gallium; the volume of mesopores in the molecular sieve represents 40-70% by volume of the total pore volume of the molecular sieve, the volume of mesopores and the total pore volume of the molecular sieve are measured by a nitrogen adsorption BET specific surface area method, and the volume of mesopores means the pore volume of the pores having a diameter of more than 2 nm and less than 100 nm.

8. The process according to the exemplary scheme 7 of the fourth series, wherein the process further comprises: carrying out a first baking, washing and optionally drying treatment on the product obtained by the spray drying, to provide the catalytic cracking aid;

wherein the first baking is carried out at a baking temperature of 300-650° C. for 0.5-8 h; and the drying is carried out at a temperature of 100-200° C. for 0.5-24 h.

9. The process according to the exemplary scheme 7 of the fourth series, wherein the process further comprises: producing the rare earth- and phosphorus-containing molecular sieve of MFI structure rich in mesopores by the steps of:
a. filtering and washing a slurry of the molecular sieve of MFI structure obtained by crystallization to provide a water-washed molecular sieve; wherein, the water-washed molecular sieve has a sodium content, calculated as sodium oxide, of less than 5 wt % based on the total dry weight of the water-washed molecular sieve calculated as sodium oxide;
b. desiliconizing the water-washed molecular sieve obtained in step a in an alkaline solution, and filtering and washing to provide a base washed molecular sieve;
c. carrying out ammonium exchange treatment on the base washed molecular sieve obtained in step b to provide an ammonium exchanged molecular sieve; wherein the ammonium exchanged molecular sieve has a sodium content, calculated as sodium oxide, of less than 0.2 wt %, based on the total dry weight of the ammonium exchanged molecular sieve; and
d. carrying out a phosphorus modification treatment, a supported metal supporting treatment and a second baking treatment on the ammonium exchanged molecular sieve obtained in step c to provide the rare earth- and phosphorus-containing molecular sieve of MFI structure rich in mesopores.

10. The process according to the exemplary scheme 9 of the fourth series, wherein step d is carried out by one or more modes selected from:
mode (1): simultaneously carrying out a phosphorus modification treatment and a supporting treatment with the supported metal on the ammonium exchanged molecular sieve obtained in step c, and then carrying out a second baking treatment;
mode (2): sequentially carrying out a supporting treatment with the supported metal M1, a second baking treatment in a steam atmosphere, followed by a supporting treatment with the supported metal M2, a phosphorus modification treatment and a second baking treatment in an air atmosphere on the ammonium exchanged molecular sieve obtained in step c;
mode (3): sequentially carrying out a supporting treatment with the supported metal M1, followed by a supporting treatment with the supported metal M2, a phosphorus modification treatment and a second baking treatment on the ammonium exchanged molecular sieve obtained in step c; and
mode (4): sequentially carrying out a phosphorus modification treatment, a supporting treatment with the supported metal M2, a second baking treatment in the air atmosphere, followed by a supporting treatment with the supported metal M1 and a second baking treatment in a steam atmosphere on the ammonium exchanged molecular sieve obtained in step c.

11. The process according to the exemplary scheme 9 of the fourth series, wherein the molecular sieve of MFI structure in the slurry of the molecular sieve of MFI structure obtained by crystallization is a ZSM-5 molecular sieve, and the silica-to-alumina ratio is less than 80; and
if a slurry of the molecular sieve of MFI structure obtained by crystallization is prepared by a template method, step b further comprises the steps of: drying the water-washed molecular sieve and baking for a third time to remove the template agent, and then carrying out desiliconization treatment.

12. The process according to the exemplary scheme 9 of the fourth series, wherein in step b, the base in the alkaline solution is sodium hydroxide and/or potassium hydroxide; and the conditions for the desiliconization treatment comprise: a weight ratio of the molecular sieve calculated on a dry basis to the base and water in the alkaline solution of 1:(0.1-2):(5-15), a temperature of 10-100° C. and a duration of 0.2-4 hours.

13. The process according to the exemplary scheme 9 or 10 of the fourth series, wherein in step c, the conditions for the ammonium exchange treatment comprise: a weight ratio on a dry basis of the molecular sieve to the ammonium salt and water of 1:(0.1-1):(5-10), a temperature of 10-100° C., and a duration of 0.2-4 hours; and the ammonium salt is one or more selected from ammonium chloride, ammonium sulfate and ammonium nitrate.

14. The process according to the exemplary scheme 9 or 10 of the fourth series, wherein in step d, the phosphorus modification treatment comprises: carrying out impregnation and/or ion-exchange to the molecular sieve with at least one phosphorus-containing compound selected from phosphoric acid, diammonium hydrogen phosphate, ammonium dihydrogen phosphate and ammonium phosphate;

the supporting treatment with the supported metal comprises: supporting a compound containing a supported metal onto the molecular sieve by impregnation and/or ion exchange in a single time or in batches; and the conditions for the second baking treatment comprise: an atmosphere of air atmosphere and/or steam atmosphere, a baking temperature of 400-800° C., and a baking duration of 0.5-8 hours.

15. The process according to the exemplary scheme 7 of the fourth series, wherein the second clay is at least one selected from the group consisting of kaolin, sepiolite, attapulgite, rectorite, montmorillonite, halloysite, hydrotalcite, bentonite, and diatomaceous earth.

16. The process according to the exemplary scheme 7 of the fourth series, wherein the binder comprises a phosphorus-aluminum inorganic binder and an additional inorganic binder; and relative to 10-75 parts by weight of the rare earth- and phosphorus-containing molecular sieve of MFI structure rich in mesopores, the phosphorus-aluminum inorganic binder is used in an amount of 3-39 parts by weight on a dry basis, and the additional inorganic binders is used in an amount of 1-30 parts by weight on a dry basis; and the phosphorus-aluminum inorganic binder is an aluminophosphate gel and/or a first clay-containing phosphorus-aluminum inorganic binder; and the additional inorganic binder comprises at least one of pseudo-boehmite, alumina sol, silica-alumina sol and water glass.

17. The process according to the exemplary scheme 16 of the fourth series, wherein the process further comprises: preparing the first clay-containing phosphorus-aluminum inorganic binder by the steps of:

formulating an alumina source, the first clay and water into slurry, and dispersing the slurry into a slurry with a solid content of 5-48 wt %; wherein the alumina source is aluminum hydroxide and/or alumina capable of being peptized by an acid, and the first clay is used in an amount of more than 0 part by weight and not more than 40 part by weight relative to 15-40 part by weight of the alumina source calculated as $Al_2O_3$; and adding concentrated phosphoric acid into the slurry at a weight ratio of P/Al=1-6 under stirring, and reacting the mixed slurry for 15-90 minutes at 50-99° C.;

wherein in the P/Al, P represents the weight of phosphorus in the phosphoric acid calculated as a simple substance, and Al represents the weight of aluminum in the alumina source calculated as a simple substance.

18. An exemplary scheme 18 of the fourth series according to the present invention provides a catalytic cracking aid prepared by the process according to any one of the exemplary schemes 7 to 17 of the fourth series.

19. The exemplary scheme 19 of the fourth series according to the present invention provides a method for catalytically cracking a hydrocarbon oil, comprising contacting and reacting the hydrocarbon oil with the catalytic cracking aid according to any one of the exemplary schemes 1 to 6 of the fourth series and of the exemplary scheme 18 of the fourth series.

20. The method according to the exemplary scheme 19 of the fourth series, wherein the method comprises: contacting and reacting the hydrocarbon oil with a catalytic mixture containing the catalytic cracking aid and the catalytic cracking catalyst under the condition of catalytic cracking;

wherein the catalytic mixture comprises 0.1 to 30 wt % of the catalytic cracking aid.

21. The use according to the exemplary scheme 20 or 21 of the fourth series, wherein the conditions for catalytic cracking comprise: a reaction temperature of 500-800° C.; and the hydrocarbon oil is one or more selected from crude oil, naphtha, gasoline, atmospheric residue, vacuum residue, atmospheric wax oil, vacuum wax oil, straight-run wax oil, propane light/heavy deoiling, coked wax oil, and coal liquefaction product.

The inventors of the invention have discovered unexpectedly that the hierarchical pore molecular sieve of MFI structure containing phosphorus and rare earth prepared by desiliconizing the molecular sieve of MFI structure by a chemical method, washing out sodium and then carrying out a phosphorus modification treatment and a metal supporting treatment can be used in catalytic cracking processes, useful as an active component of a catalyst or an aid.

The catalytic cracking aid provided by the invention comprising molecular sieve of MFI structure after desilication treatment is rich in mesoporous structure, is beneficial to the migration of rare earth to molecular sieve pore channels, and can strengthen the synergistic effect of the rare earth and molecular sieve acid center.

The catalytic cracking aid provided by the invention has the characteristics of strong cracking capability, good shape-selective performance, high ethylene yield and high ethylene selectivity, as well as the maintaining of relatively high yields and selectivity of propylene and BTX.

Additional features and advantages of the invention will be set forth in the detailed description which follows.

EMBODIMENTS OF THE INVENTION

The embodiments of the present invention will be described below in detail. It should be understood that the embodiments and specific examples, while indicating the preferred embodiment of the invention, are given by way of illustration and explanation only, not limitation.

Molecular Sieve of MFI Structure Rich in Mesopores

According to the foregoing first aspect of the present invention, there is provided a rare earth- and phosphorus-containing molecular sieve of MFI structure rich in mesopores, the molecular sieve comprising a silicon component, an aluminum component, a phosphorus component and a supported metal component comprising supported metals M1 and M2, wherein the molecular sieve has a ratio of n($SiO_2$)/n($Al_2O_3$) of more than 15 and less than 70; the molecular sieve has a content of phosphorus, calculated as $P_2O_5$, of 1-15 wt % based on the dry weight of the molecular sieve; the molecular sieve has a supported metal content, calculated as the oxide of the supported metal, of 1-10 wt % supported metal M1 and 0.1-5 wt % supported metal M2 based on the dry weight of the molecular sieve, wherein the supported metal M1 is one or more selected from rare earth elements, preferably one or two selected from lanthanum and cerium, and the supported metal M2 is one selected from iron, cobalt, nickel, copper, manganese, zinc, tin, bismuth and gallium; the volume of mesopores in the molecular sieve represents 40-70% by volume of the total pore volume of the molecular sieve, the volume of mesopores and the total pore volume of the molecular sieve are measured by a nitrogen adsorption BET specific surface area method, and the volume of mesopores refers to the pore volume of the pores having a diameter of more than 2 nm and less than 100 nm.

Preferably, the molecular sieve of MFI structure has a ratio of n($SiO_2$)/n($Al_2O_3$) of more than 18 and less than 60; the molecular sieve has a content of phosphorus, calculated as $P_2O_5$, of 3-12 wt % based on the dry weight of the molecular sieve; the molecular sieve has a supported metal content, calculated as the oxide of the supported metal, of 3-8 wt % supported metal M1 and 0.5-3 wt % supported metal M2 based on the dry weight of the molecular sieve; and the volume of mesopores in the molecular sieve represents 45-65% by volume of the total pore volume of the molecular sieve.

The invention studies the modification to the molecular sieve catalytic material, improves the performance of promoting free radical reaction, and achieves the purpose of modulating cracking activity and product distribution by modulating the proportion of a carbonium ion route and a free radical route at the catalytic cracking temperature, so as to improve the yield and selectivity of ethylene, and simultaneously result in high outputs of propylene and BTX.

According to the invention, the RE distribution parameter, D, of the molecular sieve of MFI structure rich in mesopores preferably satisfies: 0.9≤D≤1.3, preferably 0.9≤D≤1.1, wherein D=RE (S)/RE (C), RE (S) represents the content of rare earth in any region of more than 100 $nm^2$ in a distance H inward from the edge of a crystal face of the molecular sieve crystal grain measured by a TEM-EDS method, and RE (C) represents the content of rare earth in any region of more than 100 $nm^2$ in a distance H outward from the geometric center of the crystal face of the molecular sieve crystal grain measured by a TEM-EDS method, wherein H is 10% of the distance from a certain point on the edge of the crystal face to the geometric center of the crystal face. The molecular sieve having a RE distribution parameter, D, satisfying the range above has more rare earth in the pore channel, thereby improving the yield of ethylene, propylene and BTX.

For the molecular sieve of MFI structure rich in mesopores of the present invention, it is well known for those skilled in the art to determine the rare earth content of the molecular sieve by TEM-EDS method, wherein the geometric center is also well known to those skilled in the art, and can be calculated according to a formula, which is not described herein. Generally, the geometric center of a general symmetric graph is the intersection point of the connecting lines of respective opposite vertexes. For example, the geometric center of a hexagonal crystal face of a conventional hexagonal plate-shaped ZSM-5 is positioned at the intersection point of three opposite vertexes.

Process of Producing Molecular Sieve of MFI Structure Rich in Mesopores

According to the aforementioned second aspect of the present invention, the present invention also provides a process of producing the molecular sieve of MFI structure rich in mesopores, the process comprising:

a. filtering and washing a slurry of a molecular sieve of MFI structure obtained by crystallization to provide a water-washed molecular sieve; wherein, the water-washed molecular sieve has a sodium content, calculated as sodium oxide, of less than 5 wt % based on the total dry weight of the water-washed molecular sieve calculated as sodium oxide;

b. desiliconizing the water-washed molecular sieve obtained in step a in an alkaline solution, and then filtering and washing to provide a base washed molecular sieve;

c. carrying out an ammonium exchange treatment on the base washed molecular sieve obtained in step b to provide an ammonium exchanged molecular sieve; wherein the ammonium exchanged molecular sieve has a sodium content, calculated as sodium oxide, of less than 0.2 wt %, based on the total dry weight of the ammonium exchanged molecular sieve; and d. carrying out a phosphorus modification treatment, a supporting treatment with the supported metal and a baking treatment on the ammonium exchanged molecular sieve obtained in step c to provide the rare earth- and phosphorus-containing molecular sieve of MFI structure rich in mesopores.

According to the invention, said step d may be carried out by one or more modes selected from:

mode (1): simultaneously carrying out a phosphorus modification treatment and a supporting treatment with the supported metal on the ammonium exchanged molecular sieve obtained in step c, and then carrying out a baking treatment.

mode (2): the supported metals M1 and M2 being respectively used for treatment, and the baking treatment comprising a baking treatment in a steam atmosphere and a baking treatment in an air atmosphere, wherein the ammonium exchanged molecular sieve obtained in step c is sequentially subjected to a supporting treatment with the supported metal M1, a baking treatment in a steam atmosphere, followed by a supporting treatment with the supported metal M2, a phosphorus modification treatment and a baking treatment in the air atmosphere;

mode (3): the supported metals M1 and M2 being respectively used for treatment, and sequentially carrying out a supporting treatment with the supported metal M1, followed by a supporting treatment with the supported metal M2, a phosphorus modification treatment and a baking treatment on the ammonium exchanged molecular sieve obtained in step c;

mode (4): the supported metals M1 and M2 being respectively used for treatment, and the baking treatment comprising a baking treatment in a steam atmosphere and a baking in an air atmosphere, wherein the ammonium exchanged molecular sieve obtained in step c is sequentially subjected to a phosphorus modification treatment, a supporting treatment with the supported metal M2 and a baking treatment in the air atmosphere, followed by a supporting treatment with the supported metal M1 and a baking treatment in a steam atmosphere.

According to the present invention, a slurry of the molecular sieve of MFI structure obtained by crystallization is well known to those skilled in the art, and may be obtained by amine-free crystallization, or may be a molecular sieve slurry prepared by a template method. For example, the molecular sieve of MFI structure in the slurry of the molecular sieve of MFI structure obtained by crystallization is a ZSM-5 molecular sieve, having a silica-to-alumina ratio of less than 80. It should be noted that, if a slurry of the molecular sieve of MFI structure obtained by crystallization is prepared by a template method, step b may further comprise: carrying out drying and a baking on the water-washed molecular sieve to remove the template agent, before the desilication treatment, wherein the temperatures for the drying and baking are well known to those skilled in the art and are not described in detail.

According to the present invention, the alkaline solution in step b is well known to the person skilled in the art, and may for example be an aqueous solution of an inorganic base, such as an aqueous solution of sodium hydroxide and/or potassium hydroxide. The conditions for the desiliconization treatment may comprise: a weight ratio of the molecular sieve calculated on a dry basis to the base and water in the alkaline solution of 1:(0.1-2):(5-15), a temperature of from room temperature to 100° C., and a duration of 0.2-4 hours.

According to the present invention, in step c, the ammonium exchange treatment is well known to those skilled in the art. For example, the ammonium exchange treatment comprises treating the base washed molecular sieve with an aqueous solution of an ammonium salt. The conditions for the ammonium exchange treatment comprise: a weight ratio on a dry basis of the molecular sieve to the ammonium salt and water of 1:(0.1-1):(5-10), a temperature of between room temperature and 100° C., and a duration of 0.2-4 hours, and the ammonium salt can be conventional inorganic ammonium salt, such as one or more selected from ammonium chloride, ammonium sulfate and ammonium nitrate.

According to the present invention, in step d, the phosphorus modification treatment is used for supporting phosphorus to the molecular sieve, and may comprise: carrying out impregnation and/or ion exchange on at least one phosphorus-containing compound selected from phosphoric acid, diammonium hydrogen phosphate, ammonium dihydrogen phosphate, and ammonium phosphate.

According to the present invention, in step d, the supporting treatment is used for supporting a metal to the molecular sieve. For example, the supporting treatment with the supported metal may comprise: supporting a compound containing a supported metal onto the molecular sieve by impregnation and/or ion exchange in a single time or in batches. The phosphorus modification treatment and the supporting treatment may be carried out together or separately.

According to the invention, in step d, the baking treatment is well known to the person skilled in the art. For example, the conditions of said baking treatment comprise: an atmosphere of air atmosphere and/or steam atmosphere, a baking temperature of 400-800° C., and a baking duration of 0.5-8 hours.

Catalytic Cracking Catalyst

According to the foregoing third aspect of the present invention, the present invention also provides a catalytic cracking catalyst, characterized in that the catalytic cracking catalyst comprises, based on the dry weight of the catalytic cracking catalyst: 0-25 wt % of a Y-type molecular sieve according to the invention; 5-75 wt % of the molecular sieve of MFI structure rich in mesopores according to the invention; 1-60 wt % of an inorganic binder comprising a phosphorus-aluminum inorganic binder and/or optionally an additional inorganic binder; and optionally from 0 to 65 wt %, or from 10 wt % to 55 wt % of a second clay.

The catalytic cracking catalyst provided by the invention has the performance of promoting free radical reaction, which achieves the purposes of modulating cracking activity and product distribution by modulating the proportion of a carbonium ion route and a free radical route at the catalytic cracking temperature; wherein the cracking catalyst, when being used for catalytically cracking hydrocarbon oil, can improve the cracking activity of hydrocarbons, result in higher yield of ethylene and selectivity of propylene, and simultaneously result in high outputs of propylene and BTX.

According to the invention, the RE distribution parameter, D, of the molecular sieve preferably satisfies: $0.9 \leq D \leq 1.3$, preferably $0.9 \leq D \leq 1.1$, wherein D=RE (S)/RE (C), RE (S) represents the content of rare earth in any region of more than 100 $nm^2$ in a distance H inward from the edge of a crystal face of the molecular sieve crystal grain measured by a TEM-EDS method, and RE (C) represents the content of rare earth in any region of more than 100 $nm^2$ in a distance H outward from the geometric center of the crystal face of the molecular sieve crystal grain measured by a TEM-EDS method, wherein H is 10% of the distance from a certain point on the edge of the crystal face to the geometric center of the crystal face. The molecular sieve pore canal with RE distribution parameter, D, satisfying the range has more rare earth, thereby improving the yield of ethylene, propylene and BTX.

Regarding the catalytic cracking catalyst of the invention, it is well known for those skilled in the art to determine the rare earth content of the molecular sieve by a TEM-EDS method, wherein the geometric center is also well known to those skilled in the art and can be obtained by calculation according to a formula, which is not described in detail herein. Generally, the geometric center of a general symmetric graph is the intersection point of the connection lines of the opposite vertexes. For example, the geometric center of the hexagonal crystal face of a conventional hexagonal plate-shaped ZSM-5 is positioned at the intersection point of three opposite vertexes.

According to the present invention, the phosphorus-aluminum inorganic binder which can be used for the inorganic binder may be a first clay-containing phosphorus-aluminum inorganic binder and/or an aluminophosphate gel.

According to a specific embodiment of the present invention, particularly for example for the I-type or II-type catalytic cracking catalyst, the phosphorus-aluminum inorganic binder comprises 10 to 40 wt % of an aluminum component calculated as $Al_2O_3$, 40 to 80 wt % of a phosphorus component calculated as $P_2O_5$, and not more than 42 wt % of a first clay calculated as dry weight, based on the dry weight of the phosphorus-aluminum inorganic binder.

Preferably, the phosphorus-aluminum inorganic binder (particularly for the I-type or II-type catalytic cracking catalyst, for example) comprises 15 to 40 wt % of an aluminum component calculated as $Al_2O_3$, 45 to 80 wt % of a phosphorus component calculated as $P_2O_5$, and 1 to 40 wt % of a first clay calculated on a dry basis; preferably, comprising 15 to 35 wt % of aluminum component calculated as $Al_2O_3$, 50 to 75 wt % of phosphorus component calculated as $P_2O_5$, and 8 to 35 wt % of first clay calculated as dry weight, and has a P/Al weight ratio of preferably 1.2 to 6.0, more preferably 2.0 to 5.0, and a pH value of preferably 1.5 to 3.0, or preferably 2.0 to 3.0.

According to another embodiment of the present invention, the phosphorus-aluminum inorganic binder may comprise 20 to 40 wt % of an aluminum component calculated as $Al_2O_3$ and 60 to 80 wt % of a phosphorus component calculated as $P_2O_5$, based on the dry weight of the phosphorus-aluminum inorganic binder.

According to the present invention, clay is well known to those skilled in the art, and the first clay may preferably comprise rectorite.

According to the present invention, the additional inorganic binder may be one or more selected from inorganic oxide binders conventionally used in catalytic cracking catalysts or catalyst binder components, other than the aluminophosphate gel and phosphorus-aluminum inorganic binder.

According to an embodiment of the present invention, particularly for the I-type catalytic cracking catalyst, for example, the catalytic cracking catalyst preferably comprises 15-70 wt %, preferably 20-60 wt %, of the rare earth- and phosphorus-containing molecular sieve of MFI structure rich in mesopores of the present invention, 5-36 wt %, preferably 5-35 wt %, of a binder, and 5-55 wt %, preferably 10-55 wt % of a second clay on a dry basis.

According to an embodiment of the present invention, particularly for the II-type catalytic cracking catalyst, the catalytic cracking catalyst comprises, on a dry basis, 5-40 wt %, preferably 5-35 wt % of a phosphorus-aluminum inorganic binder, 1.5-25 wt %, such as 1.5-20 wt % of a Y-type molecular sieve, 10-50 wt %, such as 10-45 wt % of the molecular sieve of MFI structure rich in mesopores according to the present invention, 5-55 wt %, such as 10-50 wt % of a second clay, and 5-28 wt %, preferably 5-25 wt % of an additional inorganic binder.

Regarding the catalytic cracking catalyst according to the present invention, particularly, for example, for the II-type catalytic cracking catalyst, the second clay may preferably be one of kaolin, metakaolin, and rectorite. The catalyst of the present invention, particularly, for example, for the II-type catalytic cracking catalyst, preferably comprises 5-55 wt %, such as 10 to 50 wt % of the second clay, for example, 12 to 28 wt % or 15 to 40 wt % of the second clay, based on the total weight of the catalyst.

Process of Producing the Catalytic Cracking Catalyst

According to the foregoing fourth aspect of the present invention, the present invention also provides a process of producing the catalytic cracking catalyst of the third aspect, the process comprising: mixing the molecular sieve of MFI structure rich in mesopores (or additionally the Y-type molecular sieve being also added) with a binder and optionally a second clay to formulate a slurry and formulating into a slurry, spray drying the slurry, and optionally, carrying out a third baking treatment.

According to an embodiment of the present invention, particularly for the I-type catalytic cracking catalyst, the weight ratio, on a dry basis, of the molecular sieve of MFI structure rich in mesopores to the binder and the second clay may be (5-78, or 5-75, or 8-78):(1-40):(0-65); preferably (10-75):(1-40):(0-65); or preferably (20-60):(5-35):(5-55).

According to an embodiment of the present invention, particularly for the II-type catalytic cracking catalyst, for example, the process of producing the catalytic cracking catalyst further comprises: adding a Y-type molecular sieve and mixing before formulating the slurry. The Y-type molecular sieve and the phosphorus- and metal-containing molecular sieve of MFI structure rich in mesopores are used in an amount, on a dry basis, of 6-85 wt %, more preferably 20-60 wt % based on the dry weight of the catalyst. In particular, the Y-type molecular sieve is used in an amount, on a dry basis, of 1 to 30 wt % based on the dry weight of the catalyst, and the phosphorus- and metal-containing molecular sieve of MFI structure rich in mesopores is used in an amount, on a dry basis, of 5 to 55 wt % based on the dry weight of the catalyst. Preferably, the Y-type molecular sieve and the phosphorus- and metal-containing molecular sieve of MFI structure rich in mesopores are used are used at a weight ratio of 1:4-4:0.

According to an embodiment of the present invention, particularly, for example, for the I-type catalytic cracking catalyst, the process comprises the third baking, and may further comprise: washing and optionally drying the product obtained by the third baking; wherein the third baking can be carried out at a temperature of 350-650° C., for example 400-600° C., preferably 450-550° C., for 0.5-8 h, 0.5-6 hours or 0.5-2 hours; for which the washing can be carried out by one of ammonium sulfate, ammonium chloride and ammonium nitrate, and the washing can be carried out at a temperature of 40-70° C.; and the drying treatment can be carried out at a temperature of 100-200° C., for example 100-150° C., for 0.5-24 h, for example 1-12 h.

According to an embodiment of the invention, particularly for example for the II-type catalytic cracking catalyst, the process comprises the third baking, and may further comprise: washing and optionally drying the product obtained by the third baking; wherein the third baking can be carried out at a temperature of, for example, 400-600° C., preferably 450-550° C., for 0.5-12 hours, such as 0.5-6 h or 0.5-2 h; for which the washing can be carried out by one of ammonium sulfate, ammonium chloride and ammonium nitrate, and the washing can be carried out at a temperature of 40-80° C., such as 40-70° C., and the drying treatment can be carried out at a temperature of 110-200° C., for example 110-180° C. or 120-150° C., for 0.5-24 h, preferably 0.5-18 h, for example 2-12 h.

For example, in one embodiment, the catalytic cracking catalyst of the present invention, particularly the I-type or II-type catalytic cracking catalyst, may be prepared by: mixing a binder (such as pseudo-boehmite, alumina sol, silica-alumina gel or a mixture of two or more of them) with a second clay (such as kaolin) and water (such as decationized water and/or deionized water) for formulating slurry with a solid content of 10-50 wt %, uniformly stirring, adjusting the pH of the slurry to 1-4 with an inorganic acid (such as hydrochloric acid, nitric acid, phosphoric acid or sulfuric acid), standing and aging at 20-80° C. for 0-2 hours (such as 0.3-2 hours) at the pH value, adding an alumina sol and/or silica sol, stirring for 0.5-1.5 hours to form a colloid, and then adding a molecular sieve, wherein the molecular sieve comprises the molecular sieve of MFI structure rich in mesopores and optionally a Y-type molecular sieve, forming a catalyst slurry, wherein the solid content of the catalyst slurry is 20-45 wt %, continuously stirring, and carrying out spray drying to provide the microspherical catalyst. Then, the microspherical catalyst is subjected to a first baking, for example, at 350-650° C., or 400-600° C., or 450-550° C. for 0.5-6 hours, or 0.5-2 hours, then washed by ammonium sulfate (wherein, the washing can be at a temperature of 40-70° C., a ratio of the ammonium sulfate:the microspherical catalyst:water=0.2-0.8:1:5-15 (weight ratio)) until the content of sodium oxide is less than 0.25 wt %, washed by water, filtered, and then dried.

In one embodiment of the process of producing the catalytic cracking catalyst according to the present invention, particularly for the I-type catalytic cracking catalyst, the binder comprises a phosphorus-aluminum inorganic binder and an additional inorganic binder, and the weight ratio of the rare earth- and phosphorus-containing molecular sieve of MFI structure rich in mesopores to the phosphorus-aluminum inorganic binder and the additional inorganic binder may be (10-75):(3-39):(1-30), preferably (10-75):(8-35):(5-25).

In one embodiment, particularly for the II-type catalytic cracking catalyst, the binder comprises a phosphorus-aluminum inorganic binder and an additional inorganic binder, and relative to 1-30 parts by weight on a dry basis of the Y-type molecular sieve, the phosphorus-aluminum inorganic binder may be used in an amount of 2-45 parts by weight on a dry basis; and the additional inorganic binder may be used in an amount of 1-30 parts by weight, preferably 5-25 parts by weight on a dry basis.

According to the process of producing the catalytic cracking catalyst provided by the invention, the molecular sieve of MFI structure rich in mesopores, the phosphorus-aluminum inorganic binder, the additional inorganic binder and the optional second clay can be mixed for formulating slurry, for which the sequence of feeding the raw materials is not specifically limited. For example, the phosphorus-aluminum inorganic binder, the additional inorganic binder, the molecular sieve and the second clay can be mixed (when the second clay is not contained, the relevant feeding step can be omitted) for formulating slurry, while preferably, the second clay, the molecular sieve and the additional inorganic binder are firstly mixed to provide a slurry and then added to the phosphorus-aluminum inorganic binder, which is beneficial to further improve the activity and selectivity of the catalyst.

The process of producing the catalytic cracking catalyst according to the present invention also comprises the step of spray drying the slurry obtained by producing the slurry. Methods of spray drying are well known to those skilled in the art and no particular requirement is imposed by the present invention.

According to the invention, the phosphorus-aluminum inorganic binder may be an aluminophosphate gel and/or a first clay-containing phosphorus-aluminum inorganic binder. The alumina source used to produce the first clay-containing phosphorus-aluminum inorganic binder may be at least one selected from the group consisting of ρ-alumina, x-alumina, η-alumina, γ-alumina, κ-alumina, σ-alumina, θ-alumina, gibbsite, surge, nordstrandite, diaspore, boehmite, and pseudo-boehmite, from which the aluminum component of the first clay-containing phosphorus-aluminum inorganic binder is derived.

According to the invention, the concentrated phosphoric acid used for preparing the first clay-containing phosphorus-aluminum inorganic binder may have a concentration of from 60 to 98 wt %, more preferably from 75 to 90 wt %. The phosphoric acid is preferably fed at feeding rate of 0.01 to 0.10 kg phosphoric acid/min/kg alumina source, and more preferably 0.03 to 0.07 kg of phosphoric acid/min/kg alumina source.

In the above embodiments, the introduction of the clay into the first clay-containing phosphorus-aluminum inorganic binder improves mass transfer and heat transfer between materials during the preparation process, avoiding the binder to be fixed caused by nonuniformly local instantaneous violent reaction, so as to provide a binder having a bonding performance equivalent to that of the phosphorus-aluminum inorganic binder prepared by a method without introducing the clay. In addition, the process introduces clay, particularly rectorite with a layered structure, to improve the heavy oil conversion capability by the obtained catalytic cracking catalyst or aid, and ensure that the obtained catalyst or aid having better selectivity.

Method for Catalytically Cracking a Hydrocarbon Oil Using the Catalytic Cracking Catalyst According to the foregoing fifth aspect of the present invention, the present invention also provides a method for catalytically cracking a hydrocarbon oil using the catalytic cracking catalyst of the third aspect.

The method for catalytically cracking a hydrocarbon oil using the catalytic cracking catalyst may be conventionally known in the art, for example, by contacting a hydrocarbon oil with the catalytic cracking catalyst of the present invention under catalytic cracking conditions. The catalytic cracking catalyst provided by the invention can be used for catalytic cracking of various hydrocarbon oils. The hydrocarbon oil may be one or more selected from various petroleum fractions such as crude oil, naphtha, light oil, atmospheric residue, vacuum residue, atmospheric wax oil, vacuum wax oil, straight-run wax oil, propane light/heavy deoiling, coked wax oil, and coal liquefaction product. The hydrocarbon oil may contain heavy metal impurities such as nickel and vanadium, and sulfur and nitrogen impurities. For example, in the hydrocarbon oil, the content of sulfur may be as high as 3.0 wt %, the content of nitrogen may be as high as 2.0 wt %, and the content of metal impurities such as vanadium and nickel may be as high as 3000 ppm.

The conditions under which the catalytic cracking is carried out may be conventionally known in the art, and preferably comprise: a reaction temperature of 500 to 800° C., for example 520 to 680° C.

In one embodiment, the I-type catalytic cracking catalyst can be added separately into a catalytic cracking reactor, for example, by contacting the hydrocarbon oil with the I-type catalytic cracking catalyst of the present invention under catalytic cracking conditions. In another embodiment, the I-type catalytic cracking catalyst can be used as an aid for use as a catalytic mixture with an additional conventional catalytic cracking catalyst. The I type catalytic cracking catalyst provided by the invention represents no more than 30 wt % of the total amount of the mixture, preferably 1-25 wt %, and more preferably 3-15 wt %.

In one embodiment of the invention, the content of the catalytic cracking aid in the catalytic mixture may vary within a wide range, and may be, for example, 0.1 to 30 wt %, preferably 2 to 26 wt %.

In one embodiment of the invention, when using the catalytic mixture, the conditions for catalytic cracking may be conventionally known in the art, preferably including: a reaction temperature of 500-800° C., such as 550-680° C.

EXAMPLES

The present invention will be further illustrated by the following examples, whilst the present invention is not limited thereto. The instruments and reagents used in the examples of the present invention are those conventionally used by those skilled in the art unless otherwise specified.

The effects by the catalyst on the yield, selectivity and the like of low-carbon olefins in the catalytic cracking of petroleum hydrocarbons were evaluated by a fixed bed micro-reaction. The catalyst sample prepared was aged for 17 hours at 800° C. under 100% steam on a fixed bed aging device, and was evaluated on the micro-reaction device, wherein the raw material oil was VGO or naphtha under the conditions of a reaction temperature at 620° C., a regeneration temperature at 620° C. and a catalyst-oil ratio of 3.2.

The crystallinity involved in the process of the present invention was measured by a standard method of ASTM D5758-2001 (2011) e 1.

The ratio of $n(SiO_2)/n(Al_2O_3)$, namely the silicon-aluminum ratio, involved in the process of the present invention was obtained by calculating the contents of silicon oxide and aluminum oxide, where the contents of the silicon oxide and the aluminum oxide were measured by a GB/T30905-2014 standard method.

The content of phosphorus involved in the process of the present invention was determined by a GB/T30905-2014 standard method, and the content of the supported metal was determined by the GB/T30905-2014 standard method.

The specific surface area involved in the process of the invention was determined using the GB5816 standard method.

The pore volume involved in the process of the invention was determined using the GB5816 standard method.

The sodium content involved in the process of the invention was determined by a GB/T30905-2014 standard method.

The RIPP standard method (if related) involved in the invention can be seen in "*Petrochemical Analysis Methods*", edited by YANG Cuiding et al, 1990.

The micro-activity (conversion, etc.) of the process of the invention was determined using the ASTM D5154-2010 standard method.

The D value was calculated as follows: selecting a crystal grain and a certain crystal face of the crystal grain under a Transmission Electron Microscopy to form a polygon, wherein the polygon has a geometric center, an edge and a 10% distance H from the geometric center to a certain point of the edge (different edge points and different H values); respectively selecting any one region in the inward H distance from the edge of the crystal face which was greater than 100 nm² and any one region in the outward H distance from the geometric center of the crystal face which was greater than 100 nm², measuring the content of rare earth (if two kinds of rare earth existing, measuring the total content of the rare earth), namely RE (S1) and RE (C1), calculating D1=RE (S1)/RE (C1), respectively selecting different crystal grains to measure for 5 times, and calculating the average value, provide the D value.

Some of the raw materials used in the examples had the following properties:

the pseudoboehmite was an industrial product produced by Shandong Aluminum Industry Company, having a solid content of 60 wt %; the alumina sol was an industrial product produced by Qilu Division of Sinopec catalyst Co., Ltd., having a content of $Al_2O_3$ of 21.5 wt %; the silica sol was an industrial product produced by Qilu Division of Sinopec Catalyst Co., Ltd., having a content of $SiO_2$ of 28.9 wt %, and a content of $Na_2O$ of 8.9%; the kaolin was a kaolin special for a catalytic cracking catalyst produced by Suzhou Kaolin Company, having a solid content of 78 wt %. $Fe_2O_3$ at a concentration of 2.0 wt %, having a content of $Na_2O$ of 0.03%, and a solid content of 77 wt %; the rectorite was produced by Hubei Zhongxiang Mingliu Rectorite Company, having a content of quartz sand of less than 3.5 wt %, a content of $Al_2O_3$ of 39.0 wt %, a content of $Fe_2O_3$ of 2.0 wt %, a content of $Na_2O$ of 0.03 wt %, and a solid content of 77 wt %; the SB aluminum hydroxide powder was manufactured by Condex, Germany, having an $Al_2O_3$ content of 75 wt %; the γ-alumina was manufactured by Condex, Germany, having an $Al_2O_3$ content of 95 wt %, and the hydrochloric acid, chemical purity, having concentration 36-38 wt %, was produced by Beijing Chemworks. HRY (Changling Division of Sinopec Catalyst Co., Ltd., having a content of rare earth of 10 wt %), PSRY molecular sieve (Changling Division of Sinopec Catalyst Co., Ltd.).

The following examples were provided to prepare the molecular sieve of MFI structure rich in mesopores according to the present invention and comparative examples were provided to prepare molecular sieves for comparison.

Example 1

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 9.7 g $H_3PO_4$ (having a concentration of 85 wt %), 4.6 g $Fe(NO_3)_3 \cdot 9H_2O$, and 8.1 g $La(NO_3)_3 \cdot 6H_2O$ were added, uniformly mixed, immersed, dried and baking treated in an air atmosphere at 550° C. for 2 hours. The molecular sieve MS-A was thus obtained, for which the physicochemical property data were listed in Table 1-1.

Example 2

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 5.8 g $H_3PO_4$ (having a concentration of 85 wt %), 3.1 g $Fe(NO_3)_3 \cdot 9H_2O$, and 4.9 g $Ce(NO_3)_2 \cdot 6H_2O$ were added, uniformly mixed, immersed, dried and treated in an air atmosphere at 550° C. for 2 hours. The molecular sieve MS-B was thus obtained, for which the physicochemical property data were listed in Table 1-1.

Example 3

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 11.6 g $H_3PO_4$ (having a concentration of 85 wt %), 6.2 g $Fe(NO_3)_3 \cdot 9H_2O$, 8.1 g $La(NO_3)_3 \cdot 6H_2O$ and 4.9 g $Ce(NO_3)_2 \cdot 6H_2O$ were added, uniformly mixed, immersed, dried and treated in an air atmosphere at 550° C. for 3 hours. The molecular sieve MS-C was thus obtained, for which the physicochemical property data were listed in Table 1-1.

Example 4

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 5.8 g $H_3PO_4$ (having a concentration of 85 wt %), 0.12 g $Fe(NO_3)_3 \cdot 9H_2O$ and 3.3 g $Ce(NO_3)_2 \cdot 6H_2O$ were added, uniformly mixed, immersed, dried and treated in an air atmosphere at 550° C. for 2 hours. The molecular sieve MS-D was thus obtained, for which the physicochemical property data were listed in Table 1-1.

Example 5

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 5.8 g $H_3PO_4$ (having a concentration of 85 wt %), 12.4 g $Fe(NO_3)_3 \cdot 9H_2O$ and 14.7 g $Ce(NO_3)_2 \cdot 6H_2O$ were added, uniformly mixed, immersed, dried and treated in an air atmosphere at 550° C. for 2 hours. The molecular sieve MS-E was thus obtained, for which the physicochemical property data were listed in Table 1-1.

Example 6

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 8.1 g $La(NO_3)_3 \cdot 6H_2O$ was added, uniformly mixed, immersed, dried and treated in a steam atmosphere at 550° C. for 2 hours. The molecular sieve was added with water to obtain a molecular sieve slurry with a solid content of 40 wt %. 9.7 g $H_3PO_4$ (having a concentration of 85 wt %), 4.6 g $Fe(NO_3)_3 \cdot 9H_2O$ was added, uniformly mixed, immersed, dried and treated in an air atmosphere at 550° C. for 2 hours. The molecular sieve MS-A-1 was thus obtained, for which the physicochemical property data were listed in Table 1-2.

Example 7

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 4.9 g $Ce(NO_3)_2 \cdot 6H_2O$ was added, uniformly mixed, immersed, dried and treated in a steam atmosphere at 550° C. for 2 hours. The molecular sieve was added with water to obtain a molecular sieve slurry with a solid content of 40 wt %. 5.8 g $H_3PO_4$ (having a concentration of 85 wt %), 3.1 g $Fe(NO_3)_3 \cdot 9H_2O$ was added, uniformly mixed, immersed, dried and treated in an air atmosphere at 550° C. for 2 hours. The molecular sieve MS-B-1 was thus obtained, for which the physicochemical property data were listed in Table 1-2.

Example 8

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 8.1 g $La(NO_3)_3 \cdot 6H_2O$ and 4.9 g $Ce(NO_3)_2 \cdot 6H_2O$ were added, uniformly mixed, immersed, dried and treated in a steam atmosphere at 550° C. for 2 hours. The molecular sieve was added with water to obtain a molecular sieve slurry with a solid content of 40 wt %. 11.6 g $H_3PO_4$ (having a concentration of 85 wt %), 6.2 g $Fe(NO_3)_3 \cdot 9H_2O$ was added, uniformly mixed, immersed, dried and treated in an air atmosphere at 550° C. for 2 hours. The molecular sieve MS-C-1 was thus obtained, for which the physicochemical property data were listed in Table 1-2.

Example 9

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 3.3 g $Ce(NO_3)_2 \cdot 6H_2O$ was added, uniformly mixed, immersed, dried and treated in a steam atmosphere at 550° C. for 2 hours. The molecular sieve was added with water to obtain a molecular sieve slurry with a solid content of 40 wt %. 5.8 g $H_3PO_4$ (having a concentration of 85 wt %), 0.12 g $Fe(NO_3)_3 \cdot 9H_2O$ was added, uniformly mixed, immersed, dried and treated in an air atmosphere at 550° C. for 2 hours. The molecular sieve MS-D-1 was thus obtained, for which the physicochemical property data were listed in Table 1-2.

Example 10

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 14.7 g $Ce(NO_3)_2 \cdot 6H_2O$ was added, uniformly mixed, immersed, dried and treated in a steam atmosphere at 550° C. for 2 hours. The molecular sieve was added with water to obtain a molecular sieve slurry with a solid content of 40 wt %. 5.8 g $H_3PO_4$ (having a concentration of 85 wt %), 12.4 g $Fe(NO_3)_3 \cdot 9H_2O$ was added, uniformly mixed, immersed, dried and treated in an air atmosphere at 550° C. for 2 hours. The molecular sieve MS-E-1 was thus obtained, for which the physicochemical property data were listed in Table 1-2.

Example 11

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 8.1 g $La(NO_3)_3 \cdot 6H_2O$ was added, uniformly mixed, immersed, and dried. The molecular sieve was added with water to obtain a molecular sieve slurry with a solid content of 40 wt %. 9.7 g $H_3PO_4$ (having a concentration of 85 wt %), 4.6 g $Fe(NO_3)_3 \cdot 9H_2O$ was added, uniformly mixed, immersed, dried and treated in an air atmosphere at 550° C. for 2 hours. The molecular sieve MS-A-2 was thus obtained, for which the physicochemical property data were listed in Table 1-2.

Example 12

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 9.7 g $H_3PO_4$ (having a concentration of 85 wt %), 4.6 g $Fe(NO_3)_3 \cdot 9H_2O$ was added, uniformly mixed, immersed, dried and treated in an air atmosphere at 550° C. for 2 hours. The molecular sieve was added with water to provide a molecular sieve slurry with a solid content of 40 wt %. 8.1 g $La(NO_3)_3 \cdot 6H_2O$ was added, uniformly mixed, immersed, dried and treated in a steam atmosphere at 550° C. for 2 hours. The molecular sieve MS-A-3 was thus obtained, for which the physicochemical property data were listed in Table 1-2.

Comparative Example 1

A crystallized ZSM-5 molecular sieve (produced by Qilu Division of Sinopec Catalyst Co., Ltd., synthesized by an amine-free method, $n(SiO_2)/n(Al_2O_3)=27$ was exchanged and washed by $NH_4Cl$ until the content of $Na_2O$ (on dry basis) was lower than 0.2 wt %. 50 g (dry basis) of the molecular sieve filter cake was added with water to obtain a slurry, so as to provide a molecular sieve slurry with a solid content of 40 wt %. 7.7 g $H_3PO_4$ (having a concentration of 85 wt %), 4.6 g $Fe(NO_3)_3 \cdot 9H_2O$ and 8.1 g $La(NO_3)_3 \cdot 6H_2O$ were added, uniformly mixed, immersed, dried and treated in an air atmosphere at 550° C. for 3 hours. The molecular sieve MS-DB1 was thus obtained, for which the physicochemical property data were listed in Table 1-1.

Comparative Example 2

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 9.7 g $H_3PO_4$ (having a concentration of 85 wt %) and 4.6 g $Fe(NO_3)_3 \cdot 9H_2O$ was added, uniformly mixed, immersed, dried and treated in an air atmosphere at 550° C. for 2 hours. The molecular sieve MS-DB2 was thus obtained, for which the physicochemical property data were listed in Table 1-1.

Comparative Example 3

A crystallized ZSM-5 molecular sieve (produced by Qilu Division of Sinopec Catalyst Co., Ltd., synthesized by an amine-free method, $n(SiO_2)/n(Al_2O_3)=27$ was filtered off the mother liquor, washed with water until the content of $Na_2O$ (on dry basis) was lower than 5.0 wt %, and filtered to provide a filter cake. 100 g (dry basis) of the molecular sieve was added into 1000 g of 2.0 wt % NaOH solution, heated to 65° C., reacted for 30 min, rapidly cooled to room temperature, filtered, and washed until the filtrate was neutral. Then, 800 g of water was added into the filter cake for formulating slurry, 40 g of $NH_4Cl$ was added, heated to 75° C., for exchange treatment for 1 h until the content of $Na_2O$ (on dry basis) was lower than 0.2 wt %, filtered, and washed to provide a molecular sieve filter cake. 50 g (dry basis) of the molecular sieve filter cake was added with water to obtain a slurry, so as to provide a molecular sieve slurry with a solid content of 40 wt %. 9.7 g $H_3PO_4$ (having a concentration of 85 wt %) and 8.1 g $La(NO_3)_3 \cdot 6H_2O$ was added, uniformly mixed, immersed, dried and treated in an air atmosphere at 550° C. for 2 hours. The molecular sieve MS-DB3 was thus obtained, for which the physicochemical property data were listed in Table 1-1.

TABLE 1-1

| Item | MS-A | MS-B | MS-C | MS-D | MS-E | MS-DB1 | MS-DB2 | MS-DB3 |
|---|---|---|---|---|---|---|---|---|
| Degree of crystallization/% | 50 | 52 | 48 | 52 | 49 | 49 | 62 | 51 |
| $n(SiO_2)/n(Al_2O_3)$ | 23 | 24 | 23 | 24 | 24 | 27 | 23 | 24 |
| $P_2O_5$ content/% | 10 | 6 | 12 | 6 | 6 | 8 | 10 | 10 |
| Content of supported metal M1 oxide/% | 5 | 3 | 8 | 2 | 9 | 5 | 0 | 5 |
| Content of supported metal M2 oxide/% | 1.5 | 1 | 2 | 0.2 | 4 | 1.5 | 1.5 | 0 |
| $S_{BET}/(m^2/g)$ | 315 | 332 | 304 | 333 | 306 | 300 | 335 | 325 |
| $(V_{mesopore}/V_{Total\ pore})/\%$ | 55 | 60 | 49 | 60 | 57 | 15 | 58 | 56 |
| RE distribution parameter, D | 1.28 | 1.24 | 1.30 | 1.22 | 1.35 | 2.80 | — | 1.27 |

TABLE 1-2

| Item | MS-A-1 | MS-B-1 | MS-C-1 | MS-D-1 | MS-E-1 | MS-A-2 | MS-A-3 |
|---|---|---|---|---|---|---|---|
| Degree of crystallization/% | 50 | 52 | 48 | 52 | 49 | 50 | 50 |
| $n(SiO_2)/n(Al_2O_3)$ | 23 | 24 | 23 | 24 | 24 | 23 | 23 |
| $P_2O_5$ content/% | 10 | 6 | 12 | 6 | 6 | 10 | 10 |
| Content of supported metal M1 oxide/% | 5 | 3 | 8 | 2 | 9 | 5 | 5 |
| Content of supported metal M2 oxide/% | 1.5 | 1 | 2 | 0.2 | 4 | 1.5 | 1.5 |
| $S_{BET}/(m^2/g)$ | 321 | 335 | 309 | 340 | 311 | 316 | 317 |
| $(V_{mesopore}/V_{Total\ pore})/\%$ | 57 | 62 | 50 | 62 | 59 | 56 | 58 |
| RE distribution parameter, D | 1.02 | 0.94 | 1.06 | 0.93 | 1.09 | 1.33 | 1.29 |

The following examples were provided to prepare the phosphorus-aluminum inorganic binders used in the present invention.

Example 13

This example was provided to prepare a phosphorus-aluminum inorganic binder according to the present invention.

1.91 kg of pseudoboehmite (containing $Al_2O_3$, 1.19 kg), 0.56 kg of kaolin (0.5 kg on a dry basis) and 3.27 kg of decationized water were formulated into a slurry for 30 minutes, 5.37 kg of concentrated phosphoric acid (85% by mass) was added to the slurry with stirring at a rate of 0.04 kg of phosphoric acid/min/kg of alumina source. The temperature was raised to 70° C. and the reaction was carried out at this temperature for 45 minutes, so as to provide the phosphorus-aluminum inorganic binder. The formulation of materials was shown in Table 2, and the binder Binder1 was obtained.

Examples 14 to 16

Phosphorus-aluminum inorganic binders were prepared according to the process of example 13, and the formulation of materials was as shown in Table 2, to provide binders Binder 2-4.

TABLE 2

| Examples | Example 13 | Example 14 | Example 15 | Example 16 |
|---|---|---|---|---|
| Binder No. | Binder1 | Binder2 | Binder3 | Binder4 |
| Pseudo-boehmite, kg | 1.91 | | | 1.60 |
| $Al_2O_3$, kg | 1.19 | | | 1.00 |
| SB, kg | | 0.94 | | |
| $Al_2O_3$, kg | | 0.70 | | |
| $\gamma$-$Al_2O_3$, kg | | | 0.58 | |
| $Al_2O_3$, kg | | | 0.58 | |
| Rectorite, kg | | 1.28 | 1.93 | |
| Dry basis, kg | | 1.00 | 1.50 | |
| Kaolin, kg | 0.56 | | | |
| Dry basis, kg | 0.50 | | | |
| Phosphoric acid, kg | 5.37 | 5.36 | 4.03 | 6.50 |
| $P_2O_5$, kg | 3.31 | 3.30 | 2.92 | 4.0 |
| Decationized water, kg | 3.27 | 6.71 | 20.18 | 4.40 |
| Total amount, kg | 11.11 | 14.29 | 25.00 | 12.5 |
| Total dry basis, kg | 5.00 | 5.00 | 5.00 | 5.00 |
| Solid content of binder, kg/kg | 0.45 | 0.35 | 0.20 | 0.40 |
| P/Al | 2.29 | 3.89 | 4.19 | 3.30 |
| $Al_2O_3$, wt % | 23.82 | 14.00 | 11.53 | 20.00 |
| $P_2O_5$, wt % | 66.18 | 66.00 | 58.47 | 80.00 |
| First clay, wt % | 10.00 | 20.00 | 30.00 | 0.00 |
| pH value | 2.20 | 2.37 | 1.75 | 2.46 |

The following examples were provided to prepare the catalytic cracking catalysts of the present invention, and the following comparative examples 4-1, 5-1 and 6-1 were provided to prepare comparative catalytic cracking catalysts.

Example 17-1

A molecular sieve MS-A, Y-type molecular sieve (PSRY molecular sieve), kaolin and pseudo-boehmite were added with decationized water and alumina sol for formulating slurry for 120 minutes, to provide a slurry with a solid content of 30 wt %. Hydrochloric acid was added to adjust the pH value of the slurry to be 3.0, and then continued to formulate the slurry for 45 minutes. Then the phosphorus-aluminum inorganic binder prepared in example 13 was added, stirred for 30 minutes, and the slurry obtained was spray-dried to provide microspheres. The microspheres were baked at 500° C. for 1 hour to provide C1, for which the formulation was shown in Table 3-1.

Comparative Examples 4-1, 5-1 and 6-1

Catalytic cracking catalysts were prepared according to the process as described in example 17-1, except that molecular sieves MS-DB1, MS-DB2 and MS-DB3 were used in place of MS-A, respectively, to provide DC1, DC2 and DC3, for which the formulations were shown in Table 3-1.

Example 18-1

A molecular sieve MS-B, Y-type molecular sieve (PSRY molecular sieve), kaolin and pseudo-boehmite were added with decationized water and alumina sol for formulating slurry for 120 minutes, to provide a slurry with a solid content of 30 wt %. Hydrochloric acid was added to adjust the pH value of the slurry to be 3.0, and then continued to formulate the slurry for 45 minutes. Then the phosphorus-aluminum inorganic binder prepared in example 14 was added, stirred for 30 minutes, and the slurry obtained was spray-dried to provide microspheres. The microspheres were baked at 500° C. for 1 hour to provide C2, for which the formulation was shown in Table 3-1.

Example 19-1

A molecular sieve MS-C, Y-type molecular sieve (HRY molecular sieve), kaolin and pseudo-boehmite were added with decationized water and alumina sol for formulating slurry for 120 minutes, to provide a slurry with a solid content of 30 wt %. Hydrochloric acid was added to adjust the pH value of the slurry to be 3.0, and then continued to formulate the slurry for 45 minutes. Then the phosphorus-aluminum inorganic binder prepared in example 15 was added, stirred for 30 minutes, and the slurry obtained was spray-dried to provide microspheres. The microspheres were baked at 500° C. for 1 hour to provide C3, for which the formulation was shown in Table 3-1.

Example 20-1

A molecular sieve MS-A, Y-type molecular sieve (PSRY molecular sieve), kaolin and pseudo-boehmite were added with decationized water and silica sol for formulating slurry for 120 minutes, to provide a slurry with a solid content of 30 wt %. Hydrochloric acid was added to adjust the pH value of the slurry to be 3.0, and then continued to formulate the slurry for 45 minutes. Then the phosphorus-aluminum inorganic binder prepared in example 13 was added, stirred for 30 minutes, and the slurry obtained was spray-dried to provide microspheres. The microspheres were baked at 500° C. for 1 hour to provide C4, for which the formulation was shown in Table 3-1.

Example 21-1

A molecular sieve MS-A, Y-type molecular sieve (PSRY molecular sieve) and kaolin were added with decationized water for formulating slurry for 120 minutes. Then the phosphorus-aluminum inorganic binder prepared in example 13 was added, to provide a slurry with a solid content of 30 wt %. After stirring for 30 minutes, the slurry obtained was spray-dried to provide microspheres. The microspheres were baked at 500° C. for 1 hour to provide C5, for which the formulation was shown in Table 3-1.

Example 22-1

A precursor of an inorganic oxidation binder (alumina sol) and kaolin were mixed according to the formulation of raw materials in the Table 3-1, formulated into a slurry with a solid content of 30 wt % using decationized water, and uniformly stirred. pH value of the slurry was adjusted to 2.8 using hydrochloric acid, stood and aged at 55° C. for 1 hour. A rare earth- and phosphorus-containing molecular sieve of MFI structure rich in mesopores and a Y-type molecular sieve (PSRY molecular sieve) were added to form a catalyst slurry (with a solid content of 35 wt %), continuously stirred, and spray dried to provide the microspherical catalyst. The microspherical catalyst was then baked at 500° C. for 1 hour, washed with ammonium sulfate (where ammonium sulfate: microspherical catalyst:water=0.5:1:10) at 60° C. to have a sodium oxide content of less than 0.25 wt %, rinsed with deionized water and filtered, and then dried at 110° C. to give catalyst C6, the formulation of which was shown in Table 3-1.

TABLE 3-1

| Item | | Ex. 17-1 | C.Ex. 4-1 | C.Ex. 5-1 | C.Ex. 6-1 | Ex. 18-1 | Ex. 19-1 | Ex. 20-1 | Ex. 21-1 | Ex. 22-1 |
|---|---|---|---|---|---|---|---|---|---|---|
| Catalyst No. | | C1 | DC1 | DC2 | DC3 | C2 | C3 | C4 | C5 | C6 |
| Molecular sieve, wt % | | | | | | | | | | |
| Molecular sieve of MFI structure, wt % | MS-A | 44 | | | | | | 35 | 44 | 44 |
| | MS-DB1 | | 44 | | | | | | | |
| | MS-DB2 | | | 44 | | | | | | |
| | MS-DB3 | | | | 44 | | | | | |
| | MS-B | | | | | 44 | | | | |
| | MS-C | | | | | | 40 | | | |
| Content of Y molecular sieve, wt % | PSRY | 6 | 6 | 6 | 6 | 6 | | 10 | 6 | 6 |
| | HRY | | | | | | 7 | | | |
| Clay, wt % | | | | | | | | | | |
| Kaolin clay | | 23 | 23 | 23 | 23 | 23 | 16 | 19 | 25 | 25 |
| Phosphorus-aluminum inorganic binder, wt % | | | | | | | | | | |
| Binder1 | | 18 | 18 | 18 | 18 | | | | 25 | |
| Binder2 | | | | | | 18 | | | | |
| Binder3 | | | | | | | 22 | | | |
| Binder4 | | | | | | | | 20 | | |
| Additional binder, wt % | | | | | | | | | | |
| Pseudo-boehmite, calculated as Al$_2$O$_3$ | | 5 | 5 | 5 | 5 | 5 | 10 | 6 | | |
| Aluminum sol, calculated as Al$_2$O$_3$ | | 4 | 4 | 4 | 4 | 4 | 5 | | | 25 |
| Silica sol, calculated as SiO$_2$ | | | | | | | | 10 | | |

The following examples were provided to prepare catalytic cracking aids according to the present invention, and comparative examples 4-2 to 6-2 were provided to prepare comparative catalytic cracking aids.

Example 17-2

A molecular sieve MS-A, kaolin and pseudo-boehmite were added with decationized water and alumina sol for formulating slurry for 120 minutes, to provide a slurry with a solid content of 30 wt %. Hydrochloric acid was added to adjust the pH value of the slurry to be 3.0, and then continued to formulate the slurry for 45 minutes. Then the phosphorus-aluminum inorganic binder prepared in example 13 was added, stirred for 30 minutes, and the slurry obtained was spray-dried to provide microspheres. The microspheres were baked at 500° C. for 1 hour to provide ZJ1, for which the formulation was shown in Table 3-2.

Comparative Examples 4-2, 5-2 and 6-2

Catalytic cracking aids were prepared according to example 17-2, except that molecular sieves MS-DB1, MS-DB2 and MS-DB3 were used in place of MS-A to provide DZJ1, DZJ2 and DZJ3, respectively, for which the formulations were shown in Table 3.

Example 18-2

A molecular sieve MS-B, kaolin and pseudo-boehmite were added with decationized water and alumina sol for formulating slurry for 120 minutes, to provide a slurry with a solid content of 30 wt %. Hydrochloric acid was added to adjust the pH value of the slurry to be 3.0, and then continued to formulate the slurry for 45 minutes. Then the phosphorus-aluminum inorganic binder prepared in example 14 was added, stirred for 30 minutes, and the slurry obtained was spray-dried to provide microspheres. The microspheres were baked at 500° C. for 1 hour to provide ZJ2, for which the formulation was shown in Table 3-2.

Example 19-2

A molecular sieve MS-C, kaolin and pseudo-boehmite were added with decationized water and alumina sol for formulating slurry for 120 minutes, to provide a slurry with a solid content of 30 wt %. Hydrochloric acid was added to adjust the pH value of the slurry to be 3.0, and then continued to formulate the slurry for 45 minutes. Then the phosphorus-aluminum inorganic binder prepared in example 15 was added, stirred for 30 minutes, and the slurry obtained was spray-dried to provide microspheres. The microspheres were baked at 500° C. for 1 hour to provide ZJ3, for which the formulation was shown in Table 3-2.

Example 20-2

A molecular sieve MS-A, kaolin, pseudo-boehmite and silica sol were added with decationized water for formulating slurry for 120 minutes, to provide a slurry with a solid content of 30 wt %. Hydrochloric acid was added to adjust the pH value of the slurry to be 3.0, and then continued to formulate the slurry for 45 minutes. Then the phosphorus-aluminum inorganic binder prepared in example 16 was added, stirred for 30 minutes, and the slurry obtained was spray-dried to provide microspheres. The microspheres were baked at 500° C. for 1 hour to provide ZJ4, for which the formulation was shown in Table 3-2.

Example 21-2

A molecular sieve MS-A and kaolin were added with decationized water for formulating slurry for 120 minutes. Then the phosphorus-aluminum inorganic binder prepared in example 13 was added, to provide a slurry with a solid content of 30 wt %. After stirring for 30 minutes, the slurry obtained was spray-dried to provide microspheres. The microspheres were baked at 500° C. with 1 hour to provide ZJ5, for which the formulation was shown in Table 3-2.

Example 22-2

A binder of alumina sol and kaolin were mixed according to the formulation of raw materials shown in the Table 3-2, formulated into a slurry with a solid content of 30 wt % using decationized water, and uniformly stirred. The pH value of the slurry was adjusted to 2.8 using hydrochloric acid, stood and aged for 1 hour at 55° C. A molecular sieve MS-A was added to form a catalyst slurry (with a solid content of 35 wt %), continuously stirred, and spray dried to provide the microspherical catalyst. The microspherical catalyst was then baked at 500° C. for 1 hour, washed with ammonium sulfate (where ammonium sulfate:microspherical catalyst:water=0.5:1:10) at 60° C. to a sodium oxide content of less than 0.25 wt %, rinsed with deionized water and filtered, and then dried at 110° C. to provide catalyst ZJ6, for which the formulation was shown in Tables 3-2.

TABLE 3-2

| Item | Ex. 17-2 | C.Ex. 4-2 | C.Ex. 5-2 | C.Ex. 6-2 | Ex. 18-2 | Ex. 19-2 | Ex. 20-2 | Ex. 21-2 | Ex. 22-2 |
|---|---|---|---|---|---|---|---|---|---|
| No. of aid | ZJ1 | DZJ1 | DZJ2 | DZJ3 | ZJ2 | ZJ3 | ZJ4 | ZJ5 | ZJ6 |
| Molecular sieve, wt % | | | | | | | | | |
| MS-A | 50 | | | | | | 40 | 50 | 50 |
| MS-DB1 | | 50 | | | | | | | |
| MS-DB2 | | | 50 | | | | | | |
| MS-DB3 | | | | 50 | | | | | |
| MS-B | | | | | 50 | | | | |
| MS-C | | | | | | 45 | | | |
| Clay, wt % | | | | | | | | | |
| Kaolin clay | 23 | 23 | 23 | 23 | 23 | 18 | 24 | 23 | 23 |
| Phosphorus-aluminum inorganic binder, wt % | | | | | | | | | |
| Binder1 | 18 | 18 | 18 | 18 | | | | 27 | |
| Binder2 | | | | | 18 | | | | |
| Binder3 | | | | | | 22 | | | |
| Binder4 | | | | | | | 20 | | |
| Additional binder, wt % | | | | | | | | | |
| Pseudo-boehmite, calculated as $Al_2O_3$ | 5 | 5 | 5 | 5 | 5 | 10 | 6 | | |
| Aluminum sol, calculated as $Al_2O_3$ | 4 | 4 | 4 | 4 | 4 | 5 | | | 27 |
| Silica sol, calculated as $SiO_2$ | | | | | | | 10 | | |

In the following examples, a fixed bed micro-reaction evaluation device was used to evaluate the reaction performance of the catalysts C1-C6 prepared in the examples of the invention, so as to illustrate the catalytic cracking reaction effect of the catalytic cracking catalyst provided by the invention.

Examples 23-1 to 28-1

The catalysts C1-C6 were respectively subjected to aging treatment at 800° C. under the condition of 100% steam atmosphere for 17 hours. The aged catalyst was loaded into a fixed bed micro-reactor, and the raw oil shown in Table 4 was catalytically cracked under the evaluation conditions of a reaction temperature of 620° C., a regeneration temperature of 620° C. and a catalyst-to-oil ratio of 3.2. The reaction results of the respective catalysts were shown in Table 5-1.

TABLE 4

| Item | Raw oil |
| --- | --- |
| Density (20° C.), g/cm3 | 0.9334 |
| Refraction (70 degree) | 1.5061 |
| Four components, m % | |
| Saturated hydrocarbons | 55.6 |
| Aromatic hydrocarbons | 30 |
| Gum material | 14.4 |
| Asphaltenes | <0.1 |
| Freezing point, ° C. | 34 |
| Metal content, ppm | |
| Ca | 3.9 |
| Fe | 1.1 |
| Mg (Mg) | <0.1 |
| Na (Na) | 0.9 |
| Ni | 3.1 |
| Pb | <0.1 |
| V | 0.5 |
| C m % | 86.88 |
| H m % | 11.94 |
| S m % | 0.7 |
| Carbon residue, m % | 1.77 |

Comparative examples 7-1 to 9-1 were provided to evaluate catalysts DC1, DC2 and DC3 prepared in comparative examples of the present invention in a fixed bed micro-reaction evaluation device to illustrate the comparative catalysts.

Comparative examples 7-1 to 9-1 catalytically cracked the same feed oil by the same method as in example 23-1, except that the catalysts used were DC1, DC2 and DC3, respectively, which had been subjected to the same aging process as in example 23-1. The reaction results of the respective catalysts were shown in Table 5-1.

In examples 29-1 to 34-1, the catalysts C1 to C6 were subjected to aging treatment at 800° C. in a 100% steam atmosphere for 17 hours. The aged catalyst was loaded into a fixed bed micro-reactor, and naphtha shown in Table 6 was catalytically cracked under the evaluation conditions of a reaction temperature of 620° C., a regeneration temperature of 620° C. and a catalyst-to-oil ratio of 3.2. The results of the respective catalyst reactions were shown in Table 7-1.

Comparative examples 10-1 to 12-1 were provided to evaluate catalysts DC1, DC2, and DC3 prepared in comparative examples of the present invention using a fixed bed micro-reaction evaluation device to illustrate the comparative catalysts.

Comparative examples 10-1 to 12-1 catalytically cracked the same feed oil by the same method as in example 29-1, except that the catalysts used were catalysts DC1, DC2 and DC3 which had been subjected to the same aging process as in example 29-1, respectively. The results of the respective catalyst reactions were shown in Table 7-1.

TABLE 6

| Materials | Naphtha fraction |
| --- | --- |
| Density (20° C.)/(g · m$^{-3}$) | 735.8 |
| Vapor pressure/kPa | 32 |
| Composition in mass/% | |
| Paraffin hydrocarbon | 51.01 |
| n-alkanes | 29.40 |
| Cycloalkanes | 38.24 |
| Olefins | 0.12 |
| Aromatic hydrocarbons | 10.52 |
| Distillation range/° C. | |
| First distillation | 45.5 |
| 5% | 72.5 |
| 10% | 86.7 |
| 30% | 106.5 |
| 50% | 120.0 |
| 70% | 132.7 |
| 90% | 148.5 |
| 95% | 155.2 |
| End point of distillation | 166.5 |

TABLE 5-1

| Item | Ex. 23-1 | C.Ex. 7-1 | C.Ex. 8-1 | C.Ex. 9-1 | Ex. 24-1 | Ex. 25-1 | Ex. 26-1 | Ex. 27-1 | Ex. 28-1 |
| --- | --- | --- | --- | --- | --- | --- | --- | --- | --- |
| Catalyst | C1 | DC1 | DC2 | DC3 | C2 | C3 | C4 | C5 | C6 |
| Balance of materials/%, wt % | | | | | | | | | |
| Dry gas | 23.87 | 13.18 | 15.61 | 16.43 | 20.85 | 22.98 | 18.27 | 20.47 | 25.11 |
| Liquefied gas | 32.08 | 24.52 | 29.1 | 28.01 | 31.8 | 35.45 | 30.05 | 34.12 | 29.12 |
| Gasoline | 14.66 | 28.9 | 24.14 | 24.58 | 16.61 | 13.42 | 20.34 | 14.38 | 14.87 |
| Diesel oil | 7.92 | 13.38 | 8.28 | 8.41 | 8.42 | 5.18 | 9.03 | 7.61 | 8.47 |
| Heavy oil | 3.43 | 3.97 | 4.01 | 3.79 | 3.49 | 3.93 | 5.02 | 4.55 | 5.05 |
| Coke | 18.04 | 16.05 | 18.86 | 18.78 | 18.83 | 19.04 | 17.29 | 18.87 | 17.38 |
| Ethylene yield | 12.61 | 4.86 | 6.34 | 8.09 | 11.99 | 11.03 | 9.76 | 10.01 | 13.01 |
| Propylene yield | 17.5 | 8.68 | 14.25 | 13.27 | 16.26 | 15.81 | 15.83 | 17.89 | 15.65 |
| BTX yield | 13.28 | 7.16 | 9.66 | 8.24 | 12.31 | 14.88 | 10.78 | 14.58 | 11.58 |

TABLE 7-1

| | Ex. 29-1 | C.Ex. 10-1 | C.Ex. 11-1 | C.Ex. 12-1 | Ex. 30-1 | Ex. 31-1 | Ex. 32-1 | Ex. 33-1 | Ex. 25 |
|---|---|---|---|---|---|---|---|---|---|
| Catalyst | C1 | DC1 | DC2 | DC3 | C2 | C3 | C4 | C5 | C6 |
| Cracking gas product yield/wt % | | | | | | | | | |
| Ethylene yield | 16.29 | 5.57 | 5.56 | 10.92 | 14.81 | 15.37 | 14.61 | 14.19 | 16.81 |
| Propylene yield | 20.15 | 10.25 | 15.85 | 13.17 | 18.54 | 19.00 | 18.31 | 20.33 | 17.22 |
| BTX yield | 20.47 | 10.08 | 14.82 | 13.47 | 17.27 | 19.07 | 16.51 | 20.90 | 17.80 |

As seen from the data in Tables 5-1 and 7-1, when different raw oils were catalytically cracked, the catalysts containing the ZSM-5 molecular sieve rich in mesopores and modified with rare earth, phosphorus and transition metal according to the present invention showed excellent performance of producing ethylene, propylene and BTX in high yield, wherein the yields of ethylene, propylene and BTX were the highest when a catalytic cracking catalyst containing a proper amount of aluminophosphate and an additional inorganic binder was used, while the yield of ethylene was significantly lower when a catalyst containing the molecular sieve without rare earth or phosphorus modification, or a catalyst containing the ZSM-5 molecular sieve modified with rare earth and phosphorus without a pore expansion treatment, was used. The catalyst containing the molecular sieve modified with rare earth without the transition metal modification results in relatively high yield of ethylene, but low yields of propylene or BTX.

The blank test examples and inventive examples described below used a fixed bed micro-reaction evaluation device to evaluate the reaction performance of 100% of equilibrium agent and the aids ZJ1-ZJ6 prepared by incorporating the equilibrium agent into the invention examples, so as to demonstrate the catalytic cracking reaction effect of the catalytic cracking aid provided by the invention.

Blank Test Example, and Examples 23-2 to 28-2

The aids ZJ1-ZJ6 were respectively subjected to aging treatment at 800° C. under the condition of 100% steam atmosphere for 17 hours. The aged ZJ1-ZJ6 and an industrial FCC equilibrium catalyst (a FCC equilibrium catalyst under an industrial brand of DVR-3, having a Micro-activity of 63) were respectively mixed. The mixture of the equilibrium agent and the catalyst was loaded into a fixed bed micro-reactor, and the raw oil as shown in Table 4 was catalytically cracked under the evaluation conditions of a reaction temperature of 620° C., a regeneration temperature of 620° C., and a catalyst-to-oil ratio of 3.2. The weight composition of each catalyst mixture and the reaction results were given in Table 5-2.

Comparative examples 7-2, 8-2 and 9-2 were provided to evaluate the performance of the aids DZJ1, DZJ2 and DZJ3 incorporated with the equilibrium agent prepared in the comparative examples of the present invention in a fixed bed micro-reaction evaluation device to illustrate the use of the comparative aids.

Comparative examples 7-2, 8-2 and 9-2 catalytically cracked the same feed oil by the same method as in example 23-2, except that the catalysts used were mixtures of the aids DZJ1, DZJ2 and DZJ3, respectively, which had been subjected to the same aging process as in example 23-2, with commercial FCC equilibrium catalysts. The weight composition of each catalyst mixture and the reaction results were given in Table 5-2.

TABLE 5-2

| Item | Blank test Ex. | Ex. 23-2 | C.Ex. 7-2 | C.Ex. 8-2 | C.Ex. 9-2 | Ex. 24-2 | Ex. 25-2 | Ex. 26-2 | Ex. 27-2 | Ex. 28-2 |
|---|---|---|---|---|---|---|---|---|---|---|
| Catalyst mixture | / | 10% ZJ1 | 10% DZJ1 | 10% DZJ2 | 10% DZJ3 | 10% ZJ2 | 10% ZJ3 | 10% ZJ4 | 10% ZJ5 | 10% ZJ6 |
| | 100% equil. agent | 90% equil. agent | 90% equil. agent | 90% equil. agent | 90% equil. agent | 90% equil. agent | 90% equil. agent | 90% equil. agent | 90% equil. agent | 90% equil. agent |
| Balance of materials/%, wt % | | | | | | | | | | |
| Dry gas | 8.07 | 15.07 | 10.61 | 11.43 | 12.55 | 14.38 | 14.52 | 13.48 | 14.14 | 15.48 |
| Liquefied gas | 18.54 | 29.25 | 23.28 | 26.31 | 24.42 | 28.04 | 28.10 | 26.45 | 30.98 | 27.95 |
| Gasoline | 38.28 | 26.28 | 35.14 | 31.58 | 32.61 | 27.66 | 27.98 | 30.68 | 26.08 | 27.18 |
| Diesel oil | 14.93 | 9.42 | 11.10 | 10.11 | 9.80 | 9.42 | 9.38 | 9.04 | 8.93 | 9.04 |
| Heavy oil | 11.42 | 3.94 | 9.01 | 6.79 | 6.49 | 4.57 | 3.97 | 5.93 | 3.42 | 5.42 |
| Coke | 8.76 | 16.04 | 10.86 | 13.78 | 14.13 | 15.93 | 16.05 | 14.42 | 16.45 | 14.93 |
| Ethylene yield | 1.39 | 8.75 | 2.34 | 3.59 | 4.27 | 6.37 | 7.06 | 5.57 | 7.75 | 9.21 |
| Propylene yield | 8.05 | 18.62 | 11.75 | 15.27 | 13.56 | 17.53 | 17.58 | 16.09 | 18.81 | 15.99 |
| BTX yield | 6.04 | 11.28 | 7.66 | 9.49 | 9.04 | 10.58 | 10.86 | 10.38 | 11.48 | 10.06 | equil. agent: equilibrium agent

The aids ZJ1-ZJ6 were respectively subjected to aging treatment at 800° C. under 100% steam atmosphere for 17 hours in the blank test example, and examples 29-2 to 34-2. The aged ZJ1-ZJ6 were respectively mixed with an industrial FCC equilibrium catalyst (a FCC equilibrium catalyst under an industrial brand DVR-3, having a Micro-activity of 63). The mixture of equilibrium agent and catalyst was loaded into a fixed bed microreactor and naphtha as shown in Table 6 above was catalytically cracked under the evaluation conditions of a reaction temperature of 620° C., a regeneration temperature of 620° C. and a catalyst-to-oil ratio of 3.2. The weight composition of each catalyst mixture and the reaction results were given in Table 7-2.

Comparative examples 10-2, 11-2 and 12-2 were provided to evaluate the performance of the aids DZJ1, DZJ2 and DZJ3 incorporated with the equilibrium agent prepared in the comparative examples of the present invention in a fixed bed micro-reaction evaluation device to illustrate the use of the comparative aids.

Comparative examples 10-2, 11-2 and 12-2 catalytically cracked the same feed oil by the same method as in example 29-2, except that the catalysts used were mixtures of the aids DZJ1, DZJ2 and DZJ3, respectively, which had been subjected to the same aging process as in example 29-2, with commercial FCC equilibrium catalysts. The weight composition of each catalyst mixture and the reaction results were given in Table 7-2.

TABLE 7-2

|  | Blank test Example | Ex. 29-2 | C.Ex. 10-2 | C.Ex. 11-2 | C.Ex. 12-2 | Ex. 30-2 | Ex. 31-2 | Ex. 32-2 | Ex. 33-2 | Ex. 34-2 |
|---|---|---|---|---|---|---|---|---|---|---|
| Catalyst mixture | / 100% of equil. agent | 10% ZJ1 90% of equil. agent | 10% DZJ1 90% of equil. agent | 10% DZJ2 90% of equil. agent | 10% DZJ3 90% of equil. agent | 10% ZJ2 90% of equil. agent | 10% ZJ3 90% of equil. agent | 10% ZJ4 90% of equil. agent | 10% ZJ5 90% of equil. agent | 10% ZJ6 90% of equilibrium agent |
| Cracking gas product yield/wt % |  |  |  |  |  |  |  |  |  |  |
| Ethylene yield | 2.01 | 10.32 | 5.64 | 5.92 | 6.56 | 8.92 | 9.55 | 8.61 | 8.17 | 10.88 |
| Propylene yield | 8.42 | 17.15 | 12.25 | 13.95 | 13.05 | 15.51 | 16.61 | 15.31 | 17.34 | 15.34 |
| BTX yield | 8.62 | 16.47 | 9.08 | 10.82 | 9.47 | 13.27 | 15.07 | 12.51 | 16.90 | 13.80 | equil. agent: equilibrium agent

As seen from the data in Tables 5-2 and 7-2 when different raw oils were catalytically cracked, the catalysts containing the ZSM-5 molecular sieve rich in mesopores and modified with rare earth, phosphorus and transition metal according to the present invention showed excellent performance of producing ethylene, propylene and BTX in high yield, wherein the yields of ethylene, propylene and BTX were the highest when a catalytic cracking catalyst containing a proper amount of aluminophosphate and an additional inorganic binder was used, while the yield of ethylene was significantly lower when a catalyst containing the molecular sieve without rare earth or phosphorus modification, or a catalyst containing the ZSM-5 molecular sieve modified with rare earth and phosphorus without a pore expansion treatment. The catalyst containing the molecular sieve modified with rare earth without the transition metal modification results in relatively high yield of ethylene, but low yields of propylene or BTX.

The preferred embodiments of the present invention have been described in detail above, however, the present invention is not limited to the specific details of the above embodiments, and various simple modifications may be formulated to the technical solution of the present invention within the technical idea of the present invention, and these simple modifications are all within the protection scope of the present invention.

It should be noted that, in the above embodiments, the various features described in the above embodiments may be combined in any suitable manner, and in order to avoid unnecessary repetition, the present invention does not separately describe various possible combinations.

In addition, any combination of the various embodiments of the present invention can be made, and the same should be considered as the content of the present invention as long as the idea of the present invention is not violated.

The invention claimed is:

1. A modified molecular sieve having a MFI structure, comprising phosphorus, a supported metal M1, and a supported metal M2,
    wherein the modified molecular sieve has:
        a ratio of $(SiO_2)/(Al_2O_3)$ of more than 15 and less than 70,
        a content of phosphorus, calculated as $P_2O_5$, of 1-15 wt % based on a dry weight of the modified molecular sieve,
        a content of supported metal M1, calculated as oxide of the supported metal M1, of 1-10 wt %, based on the dry weight of the modified molecular sieve, and
        a content of supported metal M2, calculated as oxide of the supported metal M2, of 0.1-5 wt %, based on the dry weight of the modified molecular sieve,
    wherein the supported metal M1 is one or more selected from rare earth elements, and the supported metal M2 is one selected from iron, cobalt, nickel, copper, manganese, zinc, tin, bismuth and gallium,
    wherein a volume of mesopores in the modified molecular sieve represents 40-70% by volume of a total pore volume of the modified molecular sieve, the volume of mesopores and the total pore volume of the modified molecular sieve are measured by a nitrogen adsorption BET specific surface area method, and the volume of mesopores is the pore volume of the pores having a diameter of more than 2 nm and less than 100 nm,
    wherein the modified molecular sieve has a RE distribution parameter, D, which satisfies $0.9 \leq D \leq 1.3$, wherein D=RE (S)/RE (C), RE (S) represents a content of rare earth in any region of more than 100 $nm^2$ in a distance H inward from an edge of a crystal face of the molecular sieve crystal grain measured by a TEM-EDS method, and RE (C) represents a content of rare earth in any region of more than 100 $nm^2$ in a distance H outward from a geometric center of the crystal face of the molecular sieve crystal grain measured by a TEM-EDS method, wherein H is 10% of the distance from a certain point on an edge of the crystal face to the geometric center of the crystal face.

2. The modified molecular sieve according to claim 1, wherein the ratio of $(SiO_2)/(Al_2O_3)$ is greater than 18 and less than 60, the content of phosphorus, calculated as $P_2O_5$, is 3-12 wt % based on the dry weight of the molecular sieve, the content of supported metal M1, calculated as the oxide of the supported metal M1, is 3-8 wt %, based on the dry weight of the molecular sieve, and the content of supported metal M2 is 0.5-3 wt %, calculated as the oxide of the supported metal M2, based on the dry weight of the molecular sieve, and the volume of mesopores in the molecular sieve represents 45-65% by volume of the total pore volume of the molecular sieve.

3. A process of producing the modified molecular sieve according to claim 1, comprising:
  a. filtering and washing a slurry containing a molecular sieve of MFI structure obtained by crystallization to provide a water-washed molecular sieve having a sodium content, calculated as sodium oxide, of less than 5 wt % based on the total dry weight of the water-washed molecular sieve calculated as sodium oxide;
  b. desiliconizing the water-washed molecular sieve obtained in step a in an alkaline solution, and then filtering and washing to provide a base washed molecular sieve;
  c. carrying out an ammonium exchange treatment on the base washed molecular sieve obtained in step b to provide an ammonium exchanged molecular sieve having a sodium content, calculated as sodium oxide, of less than 0.2 wt %, based on the total dry weight of the ammonium exchanged molecular sieve; and
  d. carrying out a phosphorus modification treatment, a supporting treatment with the supported metal M1, a supporting treatment with the supported metal M2, and a baking treatment on the ammonium exchanged molecular sieve obtained in step c to obtain the modified molecular sieve.

4. The process according to claim 3, wherein step d is carried out according to mode (1) or mode (3), wherein:
  mode (1) comprises simultaneously carrying out the phosphorus modification treatment and the supporting treatment with the supported metal M1 and the supporting treatment with the supported metal M2 on the ammonium exchanged molecular sieve obtained in step c, and then carrying out the baking treatment; and
  mode (3) comprises sequentially carrying out the supporting treatment with the supported metal M1, the supporting treatment with the supported metal M2, the phosphorus modification treatment, and the baking treatment on the ammonium exchanged molecular sieve obtained in step c.

5. The process according to claim 3, wherein the molecular sieve of MFI structure in the slurry is a ZSM-5 molecular sieve.

6. The process according to claim 3, wherein the slurry containing the molecular sieve of MFI structure is prepared by a template method.

7. The process according to claim 3, wherein in step b, the alkaline solution is an aqueous solution of sodium hydroxide and/or potassium hydroxide; and/or
  conditions for the desiliconizing step comprise: a weight ratio of the molecular sieve calculated on a dry basis to the base and water in the alkaline solution of 1:(0.1-2):(5-15), a temperature of 10-100° C., and/or a treatment duration of 0.2-4 hours.

8. The process according to claim 3, wherein in step c, the ammonium exchange treatment comprises treating the base washed molecular sieve with an aqueous solution containing an ammonium salt, and conditions for the ammonium exchange treatment comprise: a weight ratio of the molecular sieve on a dry basis to the ammonium salt and water of 1:(0.1-1):(5-10), a temperature of 10-100° C., and/or a treatment duration of 0.2-4 hours; and
  the ammonium salt is one or more selected from ammonium chloride, ammonium sulfate, and ammonium nitrate.

9. The process according to claim 3, wherein in step d, the phosphorus modification treatment comprises: carrying out impregnation and/or ion exchange with at least one phosphorus-containing compound selected from phosphoric acid, diammonium hydrogen phosphate, ammonium dihydrogen phosphate, and ammonium phosphate;
  the supporting treatment with the supported metal M1 and the supporting treatment with the supported metal M2 comprises: supporting the supported metal M1 with a compound containing the supported metal M1 and the supported metal M2 with a compound containing the supported metal M2 by impregnation and/or ion exchange in a single batch or in a plurality of batches; and
  conditions for the baking treatment comprise: an atmosphere of air atmosphere and/or steam atmosphere, a baking temperature of 400-800° C., and/or a baking duration of 0.5-8 hours.

10. A catalytic cracking catalyst, comprising, based on the dry weight of the catalytic cracking catalyst:
  5 to 75 wt % of the modified molecular sieve according to claim 1;
  1-60 wt % of an inorganic binder comprising a first inorganic binder that is a phosphorus-aluminum inorganic binder; optionally a second inorganic binder; and optionally 0 to 65 wt % of a second clay.

11. The catalytic cracking catalyst according to claim 10, wherein the catalytic cracking catalyst comprises 2-45 wt %, on a dry basis of the phosphorus-aluminum inorganic binder and not more than 30 wt % on a dry basis of the second inorganic binder, based on the dry weight of the catalytic cracking catalyst.

12. The catalytic cracking catalyst according to claim 10, wherein the phosphorus-aluminum inorganic binder is an aluminophosphate gel and/or a first clay-containing phosphorus-aluminum inorganic binder;
  the first clay-containing phosphorus-aluminum inorganic binder comprises, based on a dry weight of the first clay-containing phosphorus-aluminum inorganic binder: 15-40 wt % of an aluminum component calculated as $Al_2O_3$, 45-80 wt % of a phosphorus component calculated as $P_2O_5$, and more than 0 and not more than 40 wt % of the first clay on a dry basis, wherein the first clay-containing phosphorus-aluminum inorganic binder has a weight ratio of P/Al of 1.0-6.0, a pH value of 1-3.5, and a solid content of 15-60 wt %; and the first clay comprises at least one selected from kaolin, sepiolite, attapulgite, rectorite, montmorillonite, and diatomite; and
  the second inorganic binder comprises at least one of pseudo-boehmite, alumina sol, silica-alumina sol, and water glass.

13. The catalytic cracking catalyst according to claim 10, comprising more than 0% wt of the second clay, which is at least one selected from kaolin, sepiolite, attapulgite, rectorite, montmorillonite, halloysite, hydrotalcite, bentonite, and diatomaceous earth.

14. The catalytic cracking catalyst according to claim 10, wherein the catalytic cracking catalyst comprises:
  10-75 wt % of the modified molecular sieve;
  1-40 wt % of the inorganic binder; and
  0 to 65 wt % of the second clay.

15. The catalytic cracking catalyst according to claim 10, wherein the catalytic cracking catalyst comprises, based on a dry weight of the catalytic cracking catalyst:
   5-55 wt % of the modified molecular sieve;
   1 to 60 wt % of the inorganic binder;
   1-30 wt % of a Y-type molecular sieve; and optionally
   0 to 60 wt % of the second clay.

16. The catalytic cracking catalyst according to claim 15, wherein the Y-type molecular sieve comprises at least one selected from a USY molecular sieve, a rare earth-containing USY molecular sieve, a REY molecular sieve, a REHY molecular sieve, and an HY molecular sieve.

17. A process of producing the catalytic cracking catalyst of claim 10, comprising:
   forming a slurry comprising the modified molecular sieve, the inorganic binder, and optionally a second clay; and
   spray drying the slurry,
   wherein, relative to 5 to 75 parts by weight of the modified molecular sieve on a dry basis, an amount of the inorganic binder on a dry basis is 1 to 60 parts by weight, and an amount of the second clay on a dry basis is 0 to 65 parts by weight.

18. The process according to claim 17, wherein the phosphorus-aluminum inorganic binder comprises a first clay-containing phosphorus-aluminum inorganic binder that contains a first clay and a phosphorus-aluminium inorganic binder, and the process further comprises: preparing the first clay-containing phosphorus-aluminum inorganic binder by:
   mixing an alumina source, the first clay, and water into a slurry with a solid content of 5-48 wt %, wherein the alumina source is aluminum hydroxide and/or alumina capable of being peptized by an acid, and the first clay is used in an amount of more than 0 part by weight and not more than 40 parts by weight on a dry basis, relative to 15-40 parts by weight of the alumina source calculated as $Al_2O_3$; and
   adding concentrated phosphoric acid into the slurry at a weight ratio of P/Al=1-6 under stirring, and reacting the slurry at 50-99° C. for 15-90 minutes, wherein P represents the weight of phosphorus in the phosphoric acid calculated as an element phosphorus, and Al represents a weight of aluminum in the alumina source calculated as an elemental aluminum.

19. The process according to claim 17, wherein the slurry further comprises Y-type molecular sieves.

20. A method for catalytically cracking a hydrocarbon oil, comprising: contacting the hydrocarbon oil with the catalytic cracking catalyst according to claim 11 under catalytic cracking reaction conditions.

21. The method according to claim 20, wherein the hydrocarbon oil is one or more selected from crude oil, naphtha, gasoline, atmospheric residuum, vacuum residuum, atmospheric wax oil, vacuum wax oil, straight-run wax oil, propane light/heavy deoiling, coked wax oil, and a coal liquefaction product.

22. The method according to claim 20, wherein the hydrocarbon oil is in contact with a catalytic mixture comprising the catalytic cracking catalyst and a second catalytic cracking catalyst.

23. The method according to claim 22, wherein the catalytic cracking catalyst is present in the catalytic mixture in an amount of 0.1 to 30 wt %.

24. The modified molecular sieve according to claim 1, wherein the supported metal M1 is one or two selected from lanthanum and cerium.

25. The process according to claim 3, wherein the baking treatment in step d comprises baking in steam and baking in air, and step d is carried out according to mode (2) or mode (4), wherein:
   mode (2) comprises sequentially subjecting the ammonium exchanged molecular sieve obtained in step c to the supporting treatment with the supported metal M1, baking in a steam atmosphere, the supporting treatment with the supported metal M2, the phosphorus modification treatment, and baking in air,
   and
   mode (4) comprises sequentially subjecting the ammonium exchanged molecular sieve obtained in step c to the phosphorus modification treatment, the supporting treatment with the supported metal M2, baking in air, the supporting treatment with the supported metal M1, and baking in steam.

* * * * *